United States Patent
Axtell

(10) Patent No.: US 12,030,950 B2
(45) Date of Patent: Jul. 9, 2024

(54) TREATMENT OF MULTIPLE SCLEROSIS AND NEUROMYELITIS OPTICA

(71) Applicant: OKLAHOMA MEDICAL RESEARCH FOUNDATION, Oklahoma City, OK (US)

(72) Inventor: Robert C. Axtell, Oklahoma City, OK (US)

(73) Assignee: Oklahoma Medical Research Foundation, Oklahoma City, OK (US)

(*) Notice: Subject to any disclaimer, the term of this patent is extended or adjusted under 35 U.S.C. 154(b) by 76 days.

(21) Appl. No.: 16/582,034

(22) Filed: Sep. 25, 2019

(65) Prior Publication Data
US 2020/0017597 A1  Jan. 16, 2020

Related U.S. Application Data

(62) Division of application No. 15/320,397, filed as application No. PCT/US2015/038267 on Jun. 29, 2015, now abandoned.

(60) Provisional application No. 62/020,756, filed on Jul. 3, 2014.

(51) Int. Cl.
| | |
|---|---|
| *C07K 16/28* | (2006.01) |
| *A61K 39/395* | (2006.01) |
| *A61K 45/06* | (2006.01) |
| *G01N 33/68* | (2006.01) |

(52) U.S. Cl.
CPC ...... *C07K 16/2878* (2013.01); *A61K 39/3955* (2013.01); *A61K 45/06* (2013.01); *C07K 16/2875* (2013.01); *G01N 33/6893* (2013.01); *C07K 2317/76* (2013.01); *G01N 2800/28* (2013.01); *G01N 2800/285* (2013.01); *G01N 2800/52* (2013.01)

(58) Field of Classification Search
CPC .......... G01N 2800/285; C07K 2317/76; C07K 16/2878
See application file for complete search history.

(56) References Cited

U.S. PATENT DOCUMENTS

| | | |
|---|---|---|
| 6,774,106 B2 | 8/2004 | Theill et al. |
| 6,896,605 B2 | 5/2005 | Ohlendorf |
| 7,189,820 B2 | 3/2007 | Ruben |
| 7,276,241 B2 | 10/2007 | Schneider et al. |
| 7,842,292 B2 | 11/2010 | Broly et al. |
| 8,524,672 B2 | 9/2013 | Ambrose et al. |
| 8,784,812 B2 | 7/2014 | Broly et al. |
| 8,808,696 B2 | 8/2014 | Broly et al. |
| 8,895,705 B2 | 11/2014 | Medema et al. |
| 2007/0212733 A1* | 9/2007 | Martin ............. A61P 17/06 435/7.21 |
| 2009/0291080 A1 | 11/2009 | Gottenberg et al. |
| 2010/0239580 A1 | 9/2010 | Del Rio et al. |
| 2012/0213768 A1 | 8/2012 | Oh et al. |
| 2012/0328567 A1* | 12/2012 | Bushnell ........... G01N 33/74 424/85.6 |
| 2014/0030261 A1 | 1/2014 | Verweij |

FOREIGN PATENT DOCUMENTS

| | | |
|---|---|---|
| WO | 2009/052293 * | 4/2009 |
| WO | WO 2014/025974 | 2/2014 |
| WO | WO 2016/003876 | 1/2016 |

OTHER PUBLICATIONS

Miller et al (PNAS, 102(41):14759-64, 2005).*
Kussie et al (Journal of Immunology, 152:146-152, 1994,).*
Chen et al, (The EMBO Journal, 14(12):2784-2794, 1995).*
Colman P. M. (Research in Immunology, 145:33-36, 1994).*
Busby et al (bioRxiv preprint first posted online May 19, 2016; pp. 1-26).*
Lipman et al., ILAR Journal, 46(3):258-268, 2005.*
Campbell, A. Laboratory Techniques in Biochemistry and Molecular Biology, vol. 23, Chapter 1, 1991 see Chapter 1.*
Edwards et al. The remarkable flexibility of the human antibody repertoire;isolation of over one thousand different antibodies to a single protein, BLyS. J Mol Biol Nov. 14, 2003;334(1):103-18. (Year: 2003).*
Almagro JC, Fransson J. Humanization of antibodies. Front Biosci. Jan. 1, 2008;13:1619-33. (Year: 2008).*
Traub J et al. B Cells and Antibodies as Targets of Therapeutic Intervention in Neuromyelitis Optica Spectrum Disorders. Pharmaceuticals (Basel). Jan. 6, 2021;14(1):37. (Year: 2021).*
Parodis I et al. B Cell Therapy in Systemic Lupus Erythematosus: From Rationale to Clinical Practice. Front Med (Lausanne). Jul. 9, 2020;7:316. (Year: 2020).*
Boujedidi et al., "Reversion of obesity-induced liver inflammation by specific blockage of CXCL12/CXCR4 signaling in obese mice," *Journal of Hepatology*, vol. 56, S484, 2012.
Chen et al., "Impact of obesity control on circulating levels of endothelial progenitor cells and angiogenesis in response to ischemic stimulation," *J. Translational Medicine*, 10:86, 2012.
Jacob et al., "Current concept of neuromyelitis optica (NMO) and NMO spectrum disorders," *J. Neurol. Neurosurg. Psychiatry*, 84(8):922-930, 2013.

(Continued)

*Primary Examiner* — Aurora M Fontainhas
*Assistant Examiner* — Jennifer A Benavides
(74) *Attorney, Agent, or Firm* — Harness, Dickey & Pierce, P.L.C.

(57) ABSTRACT

The present disclosure provides for the diagnosis and prediction of neuromyelitis optica (NMO) in subject. It also provides for treatment of multiple sclerosis (MS) in a subject.

10 Claims, 16 Drawing Sheets

(56) References Cited

OTHER PUBLICATIONS

Office Communication issued in U.S. Appl. No. 15/320,397, dated Aug. 21, 2019.
Office Communication issued in U.S. Appl. No. 15/320,397, dated Feb. 7, 2019.
Office Communication issued in U.S. Appl. No. 15/320,397, dated Mach 14, 2018.
PCT International Search Report and Written Opinion issued in International Application No. PCT/US2015/038267, dated Jan. 7, 2016.
Varfolomeev et al., "APRIL-deficient mice have normal immune system development," *Molecular and Cellular Biology*, 24(3):997-1006, 2004.
Kappos et al., "Atacicept in multiple sclerosis (ATAMS): a randomised, placebo-controlled, double-blind, phase 2 trial," *Lancet Neurol.*, 13:353-63, 2014.
Bendaoud, Boutahar, et al. "BAFF, a new target for intravenous immunoglobulin in autoimmunity and cancer." Journal of clinical immunology 27.3 (2007): 257-265.
Bio-techne. Human BAFF/BLyS/TNFSF13B Antibody. Antigen Affinity-purified Polyclonal Goat IgG. Catalog No. AF124 (Rev. Jun. 6, 2018) (2 pages).
Bio-techne. Recombinant Human TACI/TNFRSF13B Fc Chimera. Catalog No. 174-TC (Rev. Feb. 6, 2018) (1 page).
G&P Biosciences, A Gene and Protein Company. Product Datasheet. Product ID TACI-Fc, SKU# FLC0225. Human TACI ECD (Extracellular Domain), Fc-Fusion, Recombinant (accessed May 24, 2021) (1 page).
Guadagnoli, Marco, et al. "Development and characterization of APRIL antagonistic monoclonal antibodies for treatment of B-cell lymphomas." Blood, The Journal of the American Society of Hematology 117.25 (2011): 6856-6865.
Huard, Bertrand, et al. "Selective APRIL blockade delays systemic lupus erythematosus in mouse." PLOS One 7.2 (2012): e31837.
Jagessar, S. Anwar, et al. "Antibodies against human BLyS and APRIL attenuate EAE development in marmoset monkeys." Journal of neuroimmune pharmacology 7.3 (2012): 557-570.

\* cited by examiner

H&E Staining of Optic Tracts

TREATMENT OF MULTIPLE SCLEROSIS AND NEUROMYELITIS OPTICA

This application is a divisional application of U.S. patent application Ser. No. 15/320,397, filed Dec. 20, 2016, which is a national phase application under 35 U.S.C. § 371 of International Application No. PCT/US2015/038267, filed Jun. 29, 2015, which claims benefit of priority to U.S. Provisional Application Ser. No. 62/020,756, filed Jul. 3, 2014. The entire contents of each of the aforementioned disclosures are hereby incorporated by reference.

This invention was made with government support under grant number NS077099 awarded by the National Institutes of Health. The government has certain rights in the invention.

BACKGROUND OF THE INVENTION

1. Field of the Invention

The present disclosure relates to fields of pathology, immunology and molecular biology. More particularly, the present invention relates to treatment of certain forms of multiple sclerosis (MS) and neuromyelitis optica (NMO).

2. Description of Related Art

In autoimmune diseases, the function of B-cells is highly nuanced. This has been illuminated by results from clinical trials of therapies that target B-cells in multiple sclerosis (MS) and systemic lupus erythematosus (SLE). Rituximab (anti-CD20), an antibody which kills B-cells, effectively reduces MS relapses. Yet, blockade of BAFF and APRIL, two cytokines critical for B-cell survival and development, with Atacicept worsened disease activity in MS patients. This unexpected result of Atacicept in MS is in contrast to the success of blocking BAFF in SLE, where anti-BAFF therapy reduced disease flares.

These confounding results from the Rituximab, Atacicept, and anti-BAFF trials in MS and SLE provide strong evidence that B-cells can have both pro-inflammatory and anti-inflammatory functions depending on the context of the autoimmune disease. In fact, there are now several studies in mice and humans that have identified regulatory B-cell subsets (Bregs) that have the capability to inhibit inflammation and autoimmunity. This paradoxical role of B-cells/BAFF/APRIL in MS compared to other autoimmune diseases is also mirrored by the function of β-interferon (IFN). In SLE and neuromyelitis optica (NMO), IFN-β exacerbates disease flares. Yet in MS, recombinant IFN-β is a widely used therapy and reduces disease activity. Strikingly, IFN-β increases BAFF and APRIL expression in MS, lupus and NMO providing more evidence for the paradoxical function of B-cells in these autoimmune diseases.

The inventor has developed two mouse models of experimental autoimmune encephalomyelitis (EAE), the animal model for MS, which differ in response to IFN-β mimicking aspects of MS and NMO. He has published that EAE induced with myelin specific T Helper 1 cells (TH1-EAE) has reduced disease activity when treated with IFN-β and therefore and therefore models IFN-β responsive MS. On the other hand, EAE induced with myelin-specific T Helper 17 cells (TH17-EAE) worsens when treated with IFN-β, modeling NMO and IFN-β non-responsive MS. The significance of this distinction is still not fully understood.

SUMMARY OF THE INVENTION

Thus, in accordance with the present disclosure, there is provided a method for treating a subject having neuromyelitis optica (NMO) comprising administering to said subject an inhibitor of B-cell activating factor (BAFF) and/or an inhibitor or proliferating inducing ligand (APRIL). The administering may comprise intravenous, intra-arterial, subcutaneous, topical or oral administration. The inhibitor or inhibitors may be administered more than once, such as chronically. The method may further comprise administering to said subject a second NMO therapy, such as a corticosteroid, an elastase inhibitor, a gro-alpha inhibitor, azathioprine plus prednisone, mycophenolate mofetil plus prednisone, Rituximab, Mitoxantrone, intravenous immunoglobulin (IVIG), and Cyclophosphamide. The subject may suffer from vision impairment, muscle impairment or both, and the subject, following treatment, may exhibit an improvement in vision impairment, muscle impairment or both. The subject may be a non-human mammal or a human.

In another embodiment, there is provided a method for treating a subject having interferon-resistant multiple sclerosis (MS) comprising administering to said subject an inhibitor of B-cell activating factor (BAFF) and/or an inhibitor or proliferating inducing ligand (APRIL). The administering may comprise intravenous, intra-arterial, subcutaneous, topical or oral administration. The inhibitor or inhibitors may be administered more than once, such as chronically. The method may further comprise administering to said subject a second MS therapy, such as a corticosteroid, an elastase inhibitor, a gro-alpha inhibitor, azathioprine plus prednisone, mycophenolate mofetil plus prednisone, Rituximab, Mitoxantrone, intravenous immunoglobulin (IVIG), and Cyclophosphamide. The subject may suffer from vision impairment, muscle impairment or both, and the subject, following treatment, may exhibit an improvement in vision impairment, muscle impairment or both. The subject may be a non-human mammal or a human.

In still another embodiment, there is provided a method of identifying a subject having multiple sclerosis (MS) that will be resistant to interferon therapy comprising (a) obtaining a sample from said subject; and (b) assessing levels of a TH17/granulocyte factor, a type 1 interferon, B-cell activating factor (BAFF) and/or proliferating inducing ligand (APRIL) in said sample, wherein a subject having elevated TH17/granulocyte factors, type 1 interferons, BAFF and/or APRIL levels will not respond to interferon therapy. The method may further comprise administering to a subject having elevated levels an inhibitor of B-cell activating factor (BAFF) and/or an inhibitor or proliferating inducing ligand (APRIL). The method may also further comprise providing a written communication of said level or levels.

The administering may comprise intravenous, intra-arterial, subcutaneous, topical or oral administration. The inhibitor or inhibitors may be administered more than once, such as chronically. The method may further comprise administering to said subject a second MS therapy, such as a corticosteroid, an elastase inhibitor, a gro-alpha inhibitor, azathioprine plus prednisone, mycophenolate mofetil plus prednisone, Rituximab, Mitoxantrone, intravenous immunoglobulin (IVIG), and Cyclophosphamide. The subject may suffer from vision impairment, muscle impairment or both, and the subject, following treatment, may exhibit an improvement in vision impairment, muscle impairment or both. The subject may be a non-human mammal or a human.

Assessing may comprise an immunoassay, mass spectrometry or RT-PCR. The TH17/granulocyte factors may be selected from the group consisting of IL-17A, IL-17F, IL-8, Gro-alpha and/or CXCL5. The type 1 interferons may include interferon-α and/or interferon-β. A TH17/granulocyte factor level may be elevated, a type 1 interferon level may be elevated, BAFF levels may be elevated, APRIL levels may be elevated, or more than one or all of a TH17/granulocyte factor, a type 1 interferon, BAFF and APRIL level are elevated.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The following drawing forms part of the present specification and are included to further demonstrate certain aspects of the present invention. The invention may be better understood by reference to one or more of these drawings in combination with the detailed description of specific embodiments presented herein.

(FIG. 1A) Disease course of mice with TH1- and TH17-induced EAE. Disease was induced by the transfer of myelin-specific TH1 or TH17 cells into healthy recipients and paralysis was monitored daily. (FIG. 1B) Quantitative PCR reveals a significant increase in mRNA expression of BAFF and APRIL in spinal cords of TH17-EAE compared to TH1-EAE. (FIG. 1C) FACS analysis of CNS infiltrating CD19+ B-cells and CD4+ T-cells in TH1- and TH17-induced EAE. (FIG. 1D) Significant increase in frequency of B-cells but not CD4+ T-cells in TH17-EAE compared to TH1-EAE.

(FIG. 2A) Mice with TH17-EAE were treated with TACI-Ig (100 μg/dose) or PBS beginning at the peak of disease. Arrows depict dosing. (FIG. 2B) FACS analysis of peripheral blood B-cells in EAE mice treated with TACI-Ig or PBS compared to healthy mice. TACI-Ig treatment restores the percentage of immature IgM$^{hi}$/IgD$^{lo}$ B-cells. (FIG. 2C) TACI-Ig significantly increases immature B-cell percentage in TH17-EAE. P-values were determined by student's T-test.

(FIG. 5A) Hematoxylin and eosin staining of optic tracks of TH1 and TH17-EAE revealed that TH17-EAE had severe inflammation. (FIG. 5B) Optokinetic tracking (visual acuity) is significantly impaired in TH17-EAE compared TH1-EAE.

(FIG. 6A) Representative flow cytometry plot of the neutrophils (CD11b+ly6G+), Macrophages (CD11b+F480+), B-cells (CD19+) and T helper cells (CD4+) infiltrating spinal cords of TH1 and TH17-EAE. (FIG. 6B) Mean percentage+/− standard error of the mean of immune cell populations in the spinal cords of TH1 and TH17 EAE. * p<0.05 was determined by a student's T-test.

(FIG. 9A) Sections from spinal cords of TH17-EAE (clinical score of 3) were stained with anti-BAFF (red) and anti-Ly6G (green) and image on a Zeiss LSM-710 confocal microscope. (FIG. 9B) FACS analysis of BAFF expression from subsets of spinal cord infiltrating cells in TH17-EAE (score 3). T-helper cells (CD4+), B-cells (B220+), Macrophage/microglia (CD11b+/GR1), Immature neutrophil/macrophages (CD11b+GR1+), neutrophils (CD11b+/GR1++).

DESCRIPTION OF ILLUSTRATIVE EMBODIMENTS

Figure 1A:
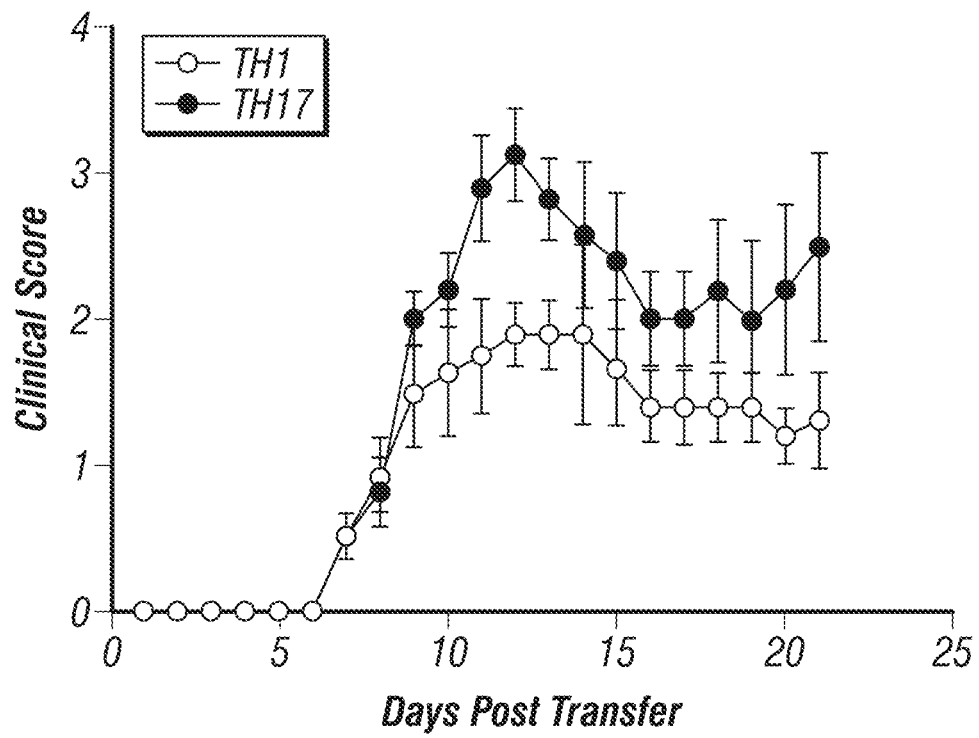
FIGS. 1A-D. Characterization of TH1 and TH17-EAE.
Figure 1B:
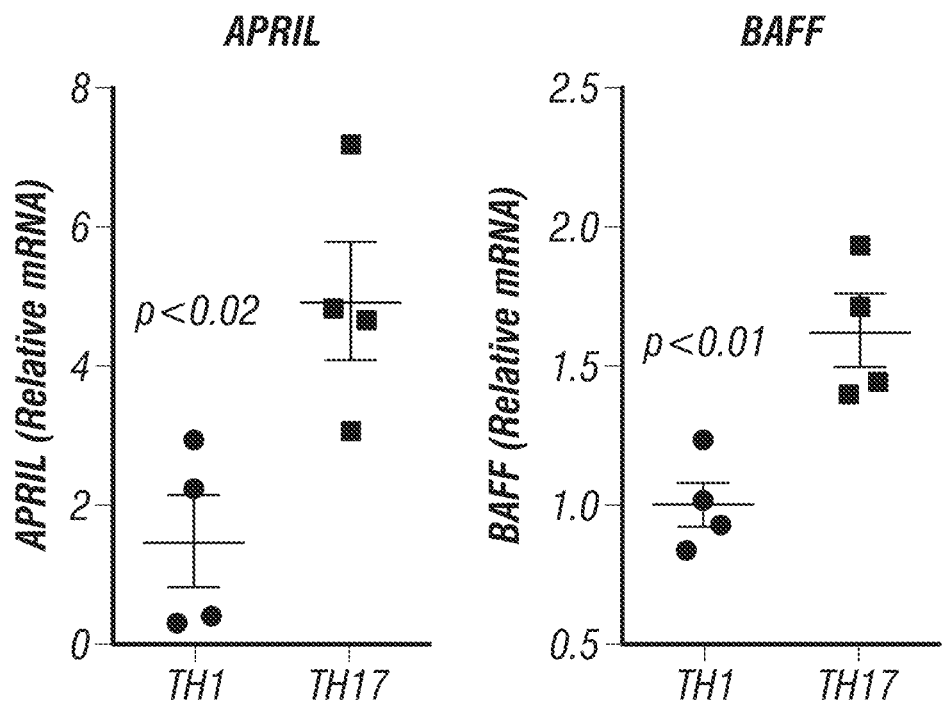
Figure 1C:
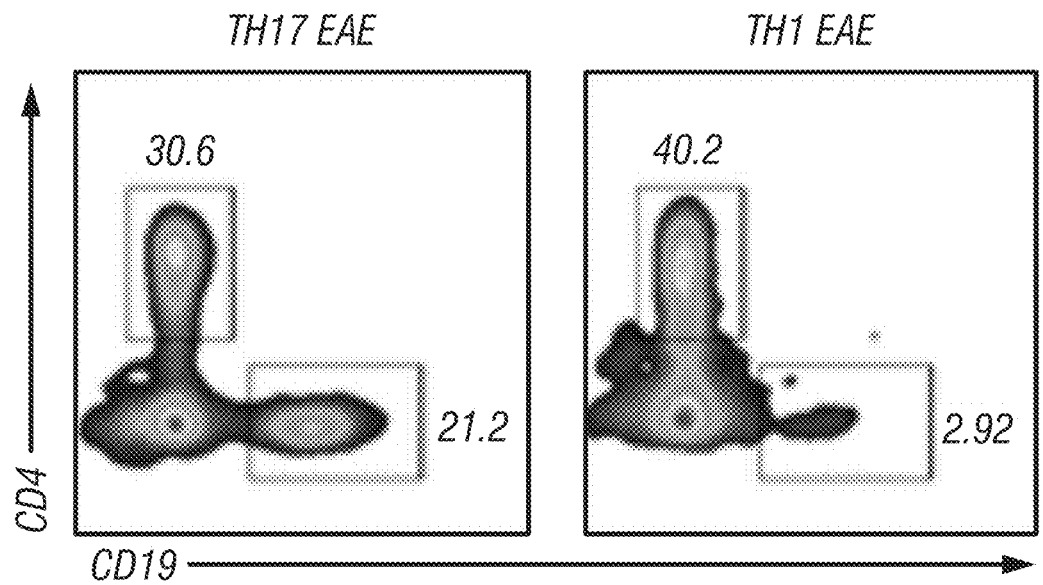
Figure 1D:
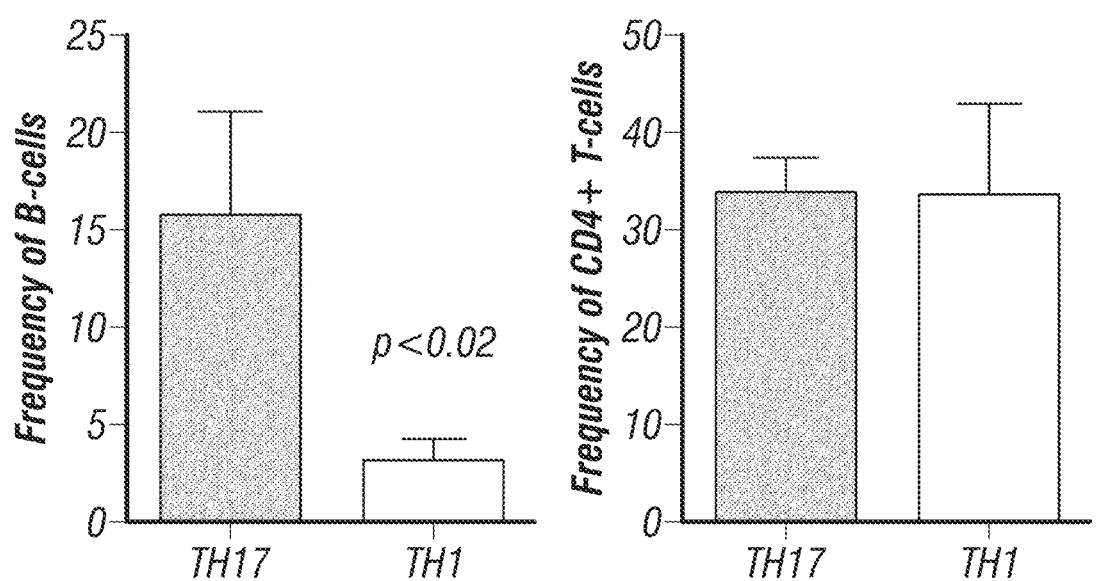

The inventor now provides, for the first time, evidence that mice with TH17-EAE have elevated expression of BAFF and APRIL and increased numbers of B-cells in inflamed spinal cords and brains as compared to mice with TH1-EAE (FIGS. 1B-D). These data suggest that BAFF, APRIL and B-cells have opposing roles in TH1 and TH17 induced EAE. This leads to the hypothesis that B-cells are pro-inflammatory in TH17-EAE, but are anti-inflammatory in TH1-EAE. Moreover, the individual functions of BAFF and APRIL in autoimmune diseases also is unclear, and these cytokines may have differential effects on inflammation in these two EAE models. These and other aspects of the disclosure are described in detail below.

1. Multiple Sclerosis

Multiple sclerosis (MS), also known as disseminated sclerosis or encephalomyelitis disseminata, is an inflammatory disease in which the insulating covers of nerve cells in the brain and spinal cord are damaged. This damage disrupts the ability of parts of the nervous system to communicate, resulting in a wide range of signs and symptoms, including physical, mental, and sometimes psychiatric problems. MS takes several forms, with new symptoms either occurring in isolated attacks (relapsing forms) or building up over time (progressive forms). Between attacks, symptoms may disappear completely; however, permanent neurological problems often occur, especially as the disease advances.

While the cause is not clear, the underlying mechanism is thought to be either destruction by the immune system or failure of the myelin-producing cells. Proposed causes for this include genetics and environmental factors such as infections. MS is usually diagnosed based on the presenting signs and symptoms and the results of supporting medical tests.

There is no known cure for multiple sclerosis. Treatments attempt to improve function after an attack and prevent new attacks. Medications used to treat MS while modestly effective can have adverse effects and be poorly tolerated. Many people pursue alternative treatments, despite a lack of evidence. The long-term outcome is difficult to predict, with good outcomes more often seen in women, those who develop the disease early in life, those with a relapsing course, and those who initially experienced few attacks. Life expectancy is 5 to 10 years lower than that of an unaffected population.

As of 2008, between 2 and 2.5 million people are affected globally with rates varying widely in different regions of the world and among different populations. The disease usually begins between the ages of 20 and 50 and is twice as common in women as in men. The name multiple sclerosis refers to scars (sclerae; better known as plaques or lesions) in particular in the white matter of the brain and spinal cord. MS was first described in 1868. A number of new treatments and diagnostic methods are under development.

A. Disease Manifestations

A person with MS can have almost any neurological symptom or sign; with autonomic, visual, motor, and sensory problems being the most common. The specific symptoms are determined by the locations of the lesions within the nervous system, and may include loss of sensitivity or changes in sensation such as tingling, pins and needles or numbness, muscle weakness, very pronounced reflexes, muscle spasms, or difficulty in moving; difficulties with coordination and balance (ataxia); problems with speech or swallowing, visual problems (nystagmus, optic neuritis or double vision), feeling tired, acute or chronic pain, and bladder and bowel difficulties, among others. Difficulties thinking and emotional problems such as depression or unstable mood are also common. Uhthoff's phenomenon, a worsening of symptoms due to exposure to higher than usual temperatures, and Lhermitte's sign, an electrical sensation that runs down the back when bending the neck, are particularly characteristic of MS. The main measure of disability and severity is the expanded disability status scale (EDSS), with other measures such as the multiple sclerosis functional composite being increasingly used in research.

The condition begins in 85% of cases as a clinically isolated syndrome over a number of days with 45% having motor or sensory problems, 20% having optic neuritis, and 10% having symptoms related to brainstem dysfunction, while the remaining 25% have more than one of the previous difficulties. The course of symptoms occurs in two main patterns initially: either as episodes of sudden worsening that last a few days to months (called relapses, exacerbations, bouts, attacks, or flare-ups) followed by improvement (85% of cases) or as a gradual worsening over time without periods of recovery (10-15% of cases). A combination of these two patterns may also occur or people may start in a relapsing and remitting course that then becomes progressive later on. Relapses are usually not predictable, occurring without warning. Exacerbations rarely occur more frequently than twice per year. Some relapses, however, are preceded by common triggers and they occur more frequently during spring and summer. Similarly, viral infections such as the common cold, influenza, or gastroenteritis increase their risk. Stress may also trigger an attack. Women with MS who become pregnant experience fewer relapses; however, during the first months after delivery the risk increases. Overall, pregnancy does not seem to influence long-term disability. Many events have not been found to affect relapse rates including vaccination, breast feeding, physical trauma, and Uhthoff's phenomenon.

The three main characteristics of MS are the formation of lesions in the central nervous system (also called plaques), inflammation, and the destruction of myelin sheaths of neurons. These features interact in a complex and not yet fully understood manner to produce the breakdown of nerve tissue and in turn the signs and symptoms of the disease. Additionally MS is believed to be an immune-mediated disorder that develops from an interaction of the individual's genetics and as yet unidentified environmental causes. Damage is believed to be caused, at least in part, by attack on the nervous system by a person's own immune system.

1. Lesions

The name multiple sclerosis refers to the scars (sclerae— better known as plaques or lesions) that form in the nervous system. These lesions most commonly affect the white matter in the optic nerve, brain stem, basal ganglia, and spinal cord, or white matter tracts close to the lateral ventricles. The function of white matter cells is to carry signals between grey matter areas, where the processing is done, and the rest of the body. The peripheral nervous system is rarely involved.

To be specific, MS involves the loss of oligodendrocytes, the cells responsible for creating and maintaining a fatty layer—known as the myelin sheath—which helps the neurons carry electrical signals (action potentials). This results in a thinning or complete loss of myelin and, as the disease advances, the breakdown of the axons of neurons. When the myelin is lost, a neuron can no longer effectively conduct electrical signals. A repair process, called remyelination, takes place in early phases of the disease, but the oligodendrocytes are unable to completely rebuild the cell's myelin sheath. Repeated attacks lead to successively less effective remyelinations, until a scar-like plaque is built up around the damaged axons. These scars are the origin of the symptoms and during an attack magnetic resonance imaging (MRI) often shows more than ten new plaques. This could indicate that there are a number of lesions below which the brain is capable of repairing itself without producing noticeable consequences. Another process involved in the creation of lesions is an abnormal increase in the number of astrocytes due to the destruction of nearby neurons. A number of lesion patterns have been described.

2. Inflammation

Apart from demyelination, the other sign of the disease is inflammation. Fitting with an immunological explanation, the inflammatory process is caused by T cells, a kind of lymphocyte that plays an important role in the body's defenses. T cells gain entry into the brain via disruptions in the blood-brain barrier. The T cells recognize myelin as foreign and attack it, explaining why these cells are also called "autoreactive lymphocytes."

The attack of myelin starts inflammatory processes, which triggers other immune cells and the release of soluble factors like cytokines and antibodies. Further breakdown of the blood-brain barrier, in turn cause a number of other damaging effects such as swelling, activation of macrophages, and more activation of cytokines and other destructive proteins. Inflammation can potentially reduce transmission of information between neurons in at least three ways. The soluble factors released might stop neurotransmission by intact neurons. These factors could lead to or enhance the loss of myelin, or they may cause the axon to break down completely.

B. Diagnosis

Multiple sclerosis is typically diagnosed based on the presenting signs and symptoms, in combination with supporting medical imaging and laboratory testing. It can be difficult to confirm, especially early on, since the signs and symptoms may be similar to those of other medical problems. The McDonald criteria, which focus on clinical, laboratory, and radiologic evidence of lesions at different times and in different areas, is the most commonly used method of diagnosis with the Schumacher and Poser criteria being of mostly historical significance. While the above criteria allow for a non-invasive diagnosis, some state that the only definitive proof is an autopsy or biopsy where lesions typical of MS are detected.

Clinical data alone may be sufficient for a diagnosis of MS if an individual has had separate episodes of neurologic symptoms characteristic of the disease. In those who seek medical attention after only one attack, other testing is needed for the diagnosis. The most commonly used diagnostic tools are neuroimaging, analysis of cerebrospinal fluid and evoked potentials. Magnetic resonance imaging of the brain and spine may show areas of demyelination (lesions or plaques). Gadolinium can be administered intravenously as a contrast agent to highlight active plaques and, by elimination, demonstrate the existence of historical lesions not associated with symptoms at the moment of the evaluation. Testing of cerebrospinal fluid obtained from a lumbar puncture can provide evidence of chronic inflammation in the central nervous system. The cerebrospinal fluid is tested for oligoclonal bands of IgG on electrophoresis, which are inflammation markers found in 75-85% of people with MS. The nervous system in MS may respond less actively to stimulation of the optic nerve and sensory nerves due to demyelination of such pathways. These brain responses can be examined using visual- and sensory-evoked potentials.

C. Standard Treatment

Although there is no known cure for multiple sclerosis, several therapies have proven helpful. The primary aims of therapy are returning function after an attack, preventing new attacks, and preventing disability. As with any medical treatment, medications used in the management of MS have several adverse effects. Alternative treatments are pursued by some people, despite the shortage of supporting evidence.

1. Acute Attacks

During symptomatic attacks, administration of high doses of intravenous corticosteroids, such as methylprednisolone, is the usual therapy, with oral corticosteroids seeming to have a similar efficacy and safety profile. Although, in general, effective in the short term for relieving symptoms, corticosteroid treatments do not appear to have a significant impact on long-term recovery. The consequences of severe attacks that do not respond to corticosteroids might be treatable by plasmapheresis.

2. Disease-Modifying Treatments

Eight disease-modifying treatments have been approved by regulatory agencies for relapsing-remitting multiple sclerosis (RRMS) including: interferon β-1a, interferon β-1b, glatiramer acetate, mitoxantrone, natalizumab, fingolimod, teriflunomide and dimethyl fumarate. Their cost effectiveness is unclear.

In RRMS they are modestly effective at decreasing the number of attacks. The interferons and glatiramer acetate are first-line treatments and are roughly equivalent, reducing relapses by approximately 30%. Early-initiated long-term therapy is safe and improves outcomes. Natalizumab reduces the relapse rate more than first-line agents; however, due to issues of adverse effects is a second-line agent reserved for those who do not respond to other treatments or with severe disease. Mitoxantrone, whose use is limited by severe adverse effects, is a third-line option for those who do not respond to other medications. Treatment of clinically isolated syndrome (CIS) with interferons decreases the chance of progressing to clinical MS. Efficacy of interferons and glatiramer acetate in children has been estimated to be roughly equivalent to that of adults. The role of some of the newer agents such as fingolimod, teriflunomide, and dimethyl fumarate, as of 2011, is not yet entirely clear.

No treatment has been shown to change the course of primary progressive MS and as of 2011 only one medication, mitoxantrone, has been approved for secondary progressive MS. In this population tentative evidence supports mitoxantrone moderately slowing the progression of the disease and decreasing rates of relapses over two years.

The disease-modifying treatments have several adverse effects. One of the most common is irritation at the injection site for glatiramer acetate and the interferons (up to 90% with subcutaneous injections and 33% with intramuscular injections). Over time, a visible dent at the injection site, due to the local destruction of fat tissue, known as lipoatrophy, may develop. Interferons may produce flu-like symptoms; some people taking glatiramer experience a post-injection reaction with flushing, chest tightness, heart palpitations, breathlessness, and anxiety, which usually lasts less than thirty minutes. More dangerous but much less common are liver damage from interferons, systolic dysfunction (12%), infertility, and acute myeloid leukemia (0.8%) from mitoxantrone, and progressive multifocal leukoencephalopathy occurring with natalizumab (occurring in 1 in 600 people treated).

Both medications and neurorehabilitation have been shown to improve some symptoms, though neither changes the course of the disease. Some symptoms have a good response to medication, such as an unstable bladder and spasticity, while others are little changed. For neurologic problems, a multidisciplinary approach is important for improving quality of life; however, it is difficult to specify a 'core team' as many different health services may be needed at different points in time. Multidisciplinary rehabilitation programs increase activity and participation of people with MS but do not influence impairment level. There is limited evidence for the overall efficacy of individual therapeutic disciplines, though there is good evidence that specific approaches, such as exercise, and psychology therapies, in particular cognitive behavioral approaches are effective.

Over 50% of people with MS may use complementary and alternative medicine, although percentages vary depending on how alternative medicine is defined. The evidence for the effectiveness for such treatments in most cases is weak or absent. Treatments of unproven benefit used by people with MS include: dietary supplementation and regimens, vitamin D, relaxation techniques such as yoga, herbal medicine (including medical *cannabis*), hyperbaric oxygen therapy, self-infection with hookworms, reflexology and acupuncture. Regarding the characteristics of users, they are more frequently women, have had MS for a longer time, tend to be more disabled and have lower levels of satisfaction with conventional healthcare.

3. Side Effects

Fingolimod may give rise to hypertension and bradycardia, macular edema, elevated liver enzymes or a reduction in lymphocyte levels. Tentative evidence supports the short term safety of teriflunomide, with common side effects including: headaches, fatigue, nausea, hair loss, and limb pain. There have also been reports of liver failure and PML with its use and it is dangerous for fetal development. Most common side effects of dimethyl fumarate are flushing and gastrointestinal problems. While dimethyl fumarate may lead to a reduction in the white blood cell count there were no reported cases of opportunistic infections during trials.

II. NEUROMYELITIS OPTICA

Neuromyelitis optica (NMO), also known as Devic's disease or Devic's syndrome, is an autoimmune, inflammatory disorder that attacks the optic nerves and spinal cord. This produces an inflammation of the optic nerve (optic neuritis) and the spinal cord (myelitis). Although inflammation may also affect the brain, the lesions are different from those observed in the related condition multiple sclerosis (MS). Spinal cord lesions lead to varying degrees of weakness or paralysis in the legs or arms, loss of sensation (including blindness), and/or bladder and bowel dysfunction. NMO is a rare disorder, which resembles MS in several ways, but requires a different course of treatment for optimal results. A likely target of the autoimmune attack at least in some patients with NMO is a protein of the nervous system cells called aquaporin 4.

NMO is similar to MS in that the body's immune system attacks the myelin surrounding nerve cells. Unlike standard MS, the attacks are not believed to be mediated by the immune system's T cells but rather by antibodies called NMO-IgG, or simply NMO antibodies. These antibodies target a protein called aquaporin 4 in the cell membranes of astrocytes, which acts as a channel for the transport of water across the cell membrane. Aquaporin 4 is found in the processes of the astrocytes that surround the blood-brain barrier, a system responsible for preventing substances in the blood from crossing into the brain. The blood-brain barrier is weakened in NMO, but it is currently unknown how the NMO-IgG immune response leads to demyelination.

A. Disease Manifestations

The main symptoms of NMO are loss of vision and spinal cord function. As for other etiologies of optic neuritis, the visual impairment usually manifests as decreased visual acuity, although visual field defects, or loss of color vision may occur in isolation or prior to formal loss of acuity. Spinal cord dysfunction can lead to muscle weakness, reduced sensation, or loss of bladder and bowel control. The typical patient has an acute and severe spastic weakness of the legs (paraparesis) or all four limbs (tetraparesis) with sensory signs, often accompanied by loss of bladder control.

As discussed above, NMO is similar to MS in that the body's immune system attacks the myelin surrounding nerve cells. Unlike standard MS, the attacks are not believed to be mediated by the immune system's T cells but rather by antibodies called NMO-IgG, or simply NMO antibodies. These antibodies target a protein called aquaporin 4 in the cell membranes of astrocytes, which acts as a channel for the transport of water across the cell membrane. Aquaporin 4 is found in the processes of the astrocytes that surround the blood-brain barrier, a system responsible for preventing substances in the blood from crossing into the brain. The blood-brain barrier is weakened in NMO, but it is currently unknown how the NMO-IgG immune response leads to demyelination.

Most research into the pathology of NMO has focused on the spinal cord. The damage in the spinal cord can range from inflammatory demyelination to necrotic damage of the white and grey matter. The inflammatory lesions in NMO have been classified as type II lesions (complement mediated demyelinization), but they differ from MS pattern II lesions in their prominent perivascular distribution. Therefore, the pattern of inflammation is often quite distinct from that seen in MS.

Approximately 20% of patients with monophasic NMO have permanent visual loss and 30% have permanent paralysis in one or more legs. Among patients with relapsing NMO, 50% have paralysis or blindness within 5 years. In some patients (33% in one study), transverse myelitis in the cervical spinal cord resulted in respiratory failure and subsequent death. However, the spectrum of NMO has widened due to improved diagnostic criteria, and the options for treatment have improved; as a result, researchers believe that these estimates will be lowered.

The prevalence and incidence of NMO has not been established partly because the disease is underrecognized and often confused with MS. NMO is more common in women than men, with women comprising over ⅔ of patients and more than 80% of those with the relapsing form of the disease. NMO is more common in Asiatic people than Caucasians. In fact, Asian optic-spinal MS (which constitutes 30% of the cases of MS in Japan) has been suggested to be identical to NMO (differences between optic-spinal and classic MS in Japanese patients). In the indigenous populations of tropical and subtropical regions, MS is rare, but when it appears it often takes the form of optic-spinal MS. The majority of NMO patients have no affected relatives, and it is generally regarded as a non-familial condition.

B. Traditional Diagnosis

The Mayo Clinic proposed a revised set of criteria for diagnosis of NMO in 2006. The new guidelines for diagnosis require two absolute criteria plus at least two of three supportive criteria being:

Absolute Criteria:
Optic neuritis
Acute myelitis
Supportive Criteria:
Brain MM not meeting criteria for MS at disease onset
Spinal cord MM with contiguous T2-weighted signal abnormality extending over 3 or more vertebral segments, indicating a relatively large lesion in the spinal cord
NMO-IgG Seropositive Status:
The NMO-IgG test checks the existence of antibodies against the aquaporin 4 antigen After the development of the NMO-IgG test, the spectrum of disorders that comprise NMO was expanded. The NMO spectrum is now believed to consist of:
  Standard NMO, according to the diagnostic criteria described above
  Limited forms of NMO, such as single or recurrent events of longitudinally extensive myelitis, and bilateral simultaneous or recurrent optic neuritis
  Asian optic-spinal MS. This variant can present CNS involvement like MS
  Longitudinally extensive myelitis or optic neuritis associated with systemic autoimmune disease
  Optic neuritis or myelitis associated with lesions in specific brain areas such as the hypothalamus, periventricular nucleus, and brainstem Whether NMO is a distinct disease or part of the wide spectrum of multiple sclerosis is debated. Recently it has been found that antiviral immune response distinguishes MS and NMO, but being MS an heterogeneous condition, as hepatitis or diabetes are, it is still possible to consider NMO part of the MS spectrum.

NMO has been associated with many systemic diseases, based on anecdoctal evidence of some NMO patients with a comorbid condition. Such conditions include: collagen vascular diseases, autoantibody syndromes, infections with varicella-zoster virus, Epstein-Barr virus, and HIV, and exposure to clioquinol and antituberculosis drugs.

C. Therapy and Prophylaxis

It may be that, on the basis of the diagnosis or prediction provided by the methods described herein, one will wish to begin, end or modify a therapeutic regimen. In particular, subjects diagnosed as having or at risk of developing NMO may be started on a therapeutic regimen. The primary aims of therapy are returning function after an attack, preventing new attacks, and preventing disability. As with any medical treatment, medications used in the management of NMO have several adverse effects, and many possible therapies are still under investigation.

Currently, there is no cure for NMO, but symptoms can be treated. Some patients recover, but many are left with impairment of vision and limbs, which can be severe. Attacks are treated with short courses of high dosage intravenous corticosteroids such as methylprednisolone IV. When attacks progress or do not respond to corticosteroid treatment, plasmapheresis can be an effective treatment. Clinical trials for these treatments contain very small numbers, and most are uncontrolled.

No controlled trials have established the effectiveness of treatments for the prevention of attacks. Many clinicians agree that long-term immunosuppression is required to reduce the frequency and severity of attacks, while others argue the exact opposite. Commonly used immunosuppressant treatments include azathioprine (Imuran) plus prednisone, mycophenolate mofetil plus prednisone, Rituximab, Mitoxantrone, intravenous immunoglobulin (IVIG), and Cyclophosphamide. The monoclonal antibody rituximab is under study. In 2007, NMO was reported to be responsive to glatiramer acetate and to low-dose corticosteroids. Normally, there is some measure of improvement in a few weeks, but residual signs and disability may persist, sometimes severely.

The disease can be monophasic, i.e., a single episode with permanent remission. However, at least 85% of patients have a relapsing form of the disease with repeated attacks of transverse myelitis and/or optic neuritis. In patients with the monophasic form the transverse myelitis and optic neuritis occur simultaneously or within days of each other. On the other hand, patients with the relapsing form are more likely to have weeks or months between the initial attacks and to have better motor recovery after the initial transverse myelitis event. Relapses usually occur early with about 55% of patients having a relapse in the first year and 90% in the first 5 years. Unlike multiple sclerosis, NMO rarely has a secondary progressive phase in which patients have increasing neurologic decline between attacks without remission. Instead, disabilities arise from the acute attacks.

III. TREATMENTS

In accordance with the present disclosure, therapeutic interventions into MS and NMO are provided. The inventor has identified the involvement of TH17-induced disease in certain types of MS, and found that these subjects are characterized by non-response to interferon therapy. NMO exhibits a similar TH17-driven disease profile. Furthermore, both of these diseases appear to be linked to increased levels of B-cell activating factor (BAFF) and proliferation-inducing ligand (APRIL). While these proteins have been shown to be viable therapeutic targets in systemic lupus erythematosus, attempts to target them in MS have failed. However, with a better understanding of the differing cytokine responses in MS subtypes, BAFF/APRIL-targeted therapies may indeed succeed, and are certainly applicable to NMO.

A. BAFF

B-cell activating factor (BAFF) also known as tumor necrosis factor ligand superfamily member 13B is a cytokine that in humans is encoded by the TNFSF13B gene. BAFF is also known as B Lymphocyte Stimulator (BLyS) and TNF- and APOL-related leukocyte expressed ligand (TALL-1) and the Dendritic cell-derived TNF-like molecule (CD257 antigen; cluster of differentiation 257). This cytokine is a ligand for receptors TNFRSF13B/TACI, TNFRSF17/BCMA, and TNFRSF13C/BAFF-R. This cytokine is expressed in B cell lineage cells, and acts as a potent B cell activator. It has been also shown to play an important role in the proliferation and differentiation of B cells. Excessive level of BAFF causes abnormally high antibody production, results in systemic lupus erythmatosis, rheumatoid arthritis, and many other autoimmune diseases.

BAFF is a 285-amino acid long peptide glycoprotein which undergoes glycosylation at residue 124. It is expressed as a membrane-bound type II transmembrane protein on various cell types including monocytes, dendritic cells and bone marrow stromal cells. The transmembrane form can be cleaved from the membrane, generating a soluble protein fragment. BAFF steady-state concentrations depend on B cells and also on the expression of BAFF-binding receptors. BAFF is the natural ligand of three unusual tumor necrosis factor receptors named BAFF-R (BR3), TACI (transmembrane activator and calcium modulator and cyclophilin ligand interactor), and BCMA (B-cell maturation antigen), all of which have differing binding affinities for it. These receptors are expressed mainly on mature B lymphocytes and their expression varies in dependence of B cell maturation (TACI is also found on a subset of T-cells and BCMA on plasma cells). BAFF-R is involved in the positive regulation during B cell development. TACI binds worst since its affinity is higher for a protein similar to BAFF, called a proliferation-inducing ligand (APRIL). BCMA displays an intermediate binding phenotype and will work with either BAFF or APRIL to varying degrees. Signaling through BAFF-R and BCMA stimulates B lymphocytes to undergo proliferation and to counter apoptosis. All these ligands act as homotrimers (i.e. three of the same molecule) interacting with homotrimeric receptors, although BAFF has been known to be active as either a hetero- or homotrimer (can aggregate into 60-mer depending on the primary structure of the protein).

B-cell activating factor has been shown to interact with TNFRSF13B, TNFSF13 and TNFRSF17. Interaction between BAFF and BAFF-R activates classical and noncanonical NF-κB signaling pathways. This interaction triggers signals essential for the formation and maintenance of B cell, thus it is important for a B-cell survival.

As an immunostimulant, BAFF (BLyS, TALL-1) is necessary for maintaining normal immunity. Inadequate level of BAFF will fail to activate B cells to produce enough immunoglobulin and will lead to immunodeficiency.

Belimumab (Benlysta) is a monoclonal antibody developed by Human Genome Sciences and GlaxoSmithKline, with significant discovery input by Cambridge Antibody Technology, which specifically recognizes and inhibits the biological activity of B-Lymphocyte stimulator (BLyS) and is in clinical trials for treatment of Systemic lupus erythematosus and other autoimmune diseases.

BAFF has been found in renal transplant biopsies with acute rejection and correlate with appearance C4d. Increased levels of BAFF may initiate aloreactive B cell and T cell immunity, therefore may promote allograft rejection. Lower levels of BAFF transcripts (or higher levels of soluble BAFF) show a higher risk of producing donor-specific antibodies in the investigated patients. Donor-specific antibodies bind with high affinity to the vascular endothelium of graft and activate complement. This process results in neutrophils infiltration, hemorrhage, fibrin deposition and platelet aggregation. Targeting BAFF-R interactions may provide new therapeutic possibilities in transplantation.

Blisibimod, a fusion protein inhibitor of BAFF, is in development by Anthera Pharmaceuticals, also primarily for the treatment of systemic lupus erythematosus.

B. APRIL

Tumor necrosis factor ligand superfamily member 13 (TNFSF13) also known as a proliferation-inducing ligand (APRIL) is a protein that in humans is encoded by the TNFSF13 gene. TNFSF13 has also been designated CD256 (cluster of differentiation 256).

The protein encoded by this gene is a member of the tumor necrosis factor ligand (TNF) ligand family. This protein is a ligand for TNFRSF17/BCMA, a member of the TNF receptor family. This protein and its receptor are both found to be important for B cell development. In vivo experiments suggest an important role for APRIL in the long-term survival of plasma cells in the bone marrow. Mice deficient in April showed a reduced ability to support plasma cell survival In vitro experiments suggested that this protein may be able to induce apoptosis through its interaction with other TNF receptor family proteins such as TNFRSF6/FAS and TNFRSF14/HVEM. Three alternatively spliced transcript variants of this gene encoding distinct isoforms have been reported. TNFSF13 has been shown to interact with TNFRSF13B and B-cell activating factor.

C. Pharmaceutical Compositions

1. Therapeutic Agents

The present disclosure envisions using variety of BAFF and APRIL inhibitors. In general, inhibitors are biological in nature (proteins, nucleic acids, carbohydrates) or synthetic (small molecules, peptoids, nucleic acid analogs, etc.). The former includes antibodies to BAFF or APRIL, and nucleic acid inhibitors (siRNAs; antisense molecules) that can be readily produced by those of skill in the art by design or preparation based on the targets themselves. The following are a few examples of biological inhibitors.

Atacicept. Atacicept is a recombinant fusion protein designed to inhibit B cells, thereby suppressing autoimmune disease. The designer protein combines the binding site for two cytokines that regulate maturation, function, and survival of B cells, B-lymphocyte stimulator (BLyS) and a proliferation-inducing ligand (APRIL), with the constant region of immunoglobin. Atacicept blocks activation of B cells by the tumor necrosis factor receptor superfamily member 13B (more commonly known as TACI), a transmembrane receptor protein found predominantly on the surface of B cells. Like the monoclonal antibody belimumab, atacicept blocks the binding of BLyS, but it also blocks APRIL. Binding of these TACI ligands induces proliferation, activation, and longevity of B cells and thus their production of autoantibodies. Atacicept is thought to selectively impair mature B cells and plasma cells with less impact on progenitor cells and memory B cells.

Studies have looked at atacicept in animal models of autoimmune disease and in patients with systemic lupus erythematosus (SLE), rheumatoid arthritis (RA), and optic neuritis. A phase II/III trial for systemic lupus erythematosus is due to run from 2008 to 2012. The subcutaneously injected protein failed a phase II trial for multiple sclerosis. The trials of atacicept in people with MS were suspended when some people taking the drug in one trial had an unexpected increase in inflammatory activity. An independent data monitoring board for the MS study found "subjects receiving atacicept were having more relapses and new Mill lesions than those on the placebo." The drug is also being studied for treatment of B-cell malignancies, including multiple myeloma, B-cell chronic lymphocytic leukemia, and non-Hodgkin's lymphoma.

Belimumab. Belimumab (trade name Benlysta) is a human monoclonal antibody that inhibits B-cell activating factor (BAFF), also known as B-lymphocyte stimulator (BLyS). B cells are responsible for part of the normal immune response, and also for the over-aggressive immune response in autoimmune diseases like systemic lupus erythematosus (SLE). Belimumab reduces the number of circulating B cells. It is possible that belimumab binds primarily to circulating soluble BAFF, therefore not inducing antibody-dependent cellular cytotoxicity that could be expected from this IgG1-type antibody.

Belimumab is approved in the United States, Canada and Europe for treatment of SLE. However, the major phase III trials excluded the more severe cases of SLE with kidney and brain damage, so its effectiveness has not been demonstrated in those cases. A Phase III study for SLE patients with kidney disease is now recruiting. U.S. FDA reviewers were concerned that belimumab is only "marginally" effective, and that there were more deaths in the treatment group. Belimumab's defenders said that in addition to its modest efficiency, belimumab allowed patients to significantly reduce their use of corticosteroids. Phase II trials of belimumab for rheumatoid arthritis were unsuccessful. Phase II trials for Sjögren's Syndrome were more successful.

While belimumab appears safe in systemic lupus erythematosus, the magnitude of benefit is small. Black/African American patients did not show a benefit. The most severe cases, with kidney and central nervous system involvement, were excluded from the trials.

The efficacy and safety of belimumab was demonstrated in 2 Phase III randomized, controlled studies, BLISS-52 and BLISS-76. The 2 studies had a total of 1,684 patients, with scores of ≥6 on the SELENA-SLEDAI assessment. They were divided into a placebo and 2 dosage groups of belimumab, in addition to standard therapy. The primary end point was a reduction of ≥4 on the SELENA-SLEDAI assessment, and several other factors, at 52 weeks. Belimumab significantly improved the response rate, reduced disease activity and severe flares, and was well tolerated. 58% had SELENA-SLEDAI scores reduced by ≥4 points during 52 weeks with belimumab 10 mg/kg compared to 46% with placebo.

Common adverse effects reported with belimumab include nausea, diarrhea, fever, as well as hypersensitivity and infusion-site reactions (severe in 0.9% of patients). It is suggested that patients be treated with an antihistamine prior to a belimumab infusion. A greater number of serious infections and deaths were reported in patients treated with belimumab than in those treated with placebo. Infections are due to the immunosuppressant properties of the drug.

Blisibimod. Blisibimod (also known as A-623, formerly AMG 623) is a selective antagonist of BAFF, being developed by Anthera Pharmaceuticals as a treatment for systemic lupus erythematosus. It is currently under active investigation in clinical trials. It is a fusion protein consisting of four BAFF binding domains fused to the N-terminus of the fragment crystallizable region (Fc) of a human antibody.

Tabalumab. Tabalumab (LY 2127399) is an anti-B-cell activating factor (BAFF) human monoclonal antibody designed for the treatment of autoimmune diseases and B cell malignancies. Tabalumab was developed by Eli Lilly and Company. A phase III clinical trial for rheumatoid arthritis was halted in February of 2013.

2. Formulations and Routes of Administration

Where therapeutic applications are contemplated, it will be necessary to prepare pharmaceutical compositions in a form appropriate for the intended application. Generally, this will entail preparing compositions that are essentially free of pyrogens, as well as other impurities that could be harmful to humans or animals.

One will generally desire to employ appropriate salts and buffers to render delivery agents stable and allow for uptake by target cells. Buffers also will be employed when recombinant cells are introduced into a patient. Aqueous compositions of the present invention comprise an effective amount of the agent, dissolved or dispersed in a pharmaceutically acceptable carrier or aqueous medium. Such compositions also are referred to as inocula. The phrases "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the agents of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. Such routes include oral, nasal, buccal, rectal, vaginal or topical route. Alternatively, administration may be by orthotopic, intradermal, subcutaneous, intramuscular, intraperitoneal, or intravenous injection. Such compositions would normally be administered as pharmaceutically acceptable compositions.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences," $15^{th}$ Ed. 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

D. Combination Therapies

It is common in many fields of medicine to treat a disease with multiple therapeutic modalities, often called "combination therapies." MS and NMO may benefit from such an approach as well. To treat these disorders using the methods and compositions of the present disclosure, one would generally contact a subject with an agent according to the present disclosure and at least one other therapy. These therapies would be provided in a combined amount effective to achieve a reduction in one or more disease parameter. This process may involve contacting the subject with the both agents/therapies at the same time, e.g., using a single composition or pharmacological formulation that includes both agents, or by contacting the subject with two distinct compositions or formulations, at the same time, wherein one composition includes the agents of the present disclosure and the other includes the other agent/therapy.

Alternatively, the agent of the present disclosure may precede or follow the other agent/treatment by intervals ranging from minutes to weeks. One would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the agent of the present disclosure or the other therapy will be desired. Various combinations may be employed, where the agent of the present disclosure is "A," and the other therapy is "B," as exemplified below:

| | | | | | |
|---|---|---|---|---|---|
| A/B/A | B/A/B | B/B/A | A/A/B | B/A/A | A/B/B |
| B/B/B/A | B/B/A/B | A/A/B/B | A/B/A/B | A/B/B/A | B/B/A/A |
| B/A/B/A | B/A/A/B | B/B/B/A | A/A/A/B | B/A/A/A | A/B/A/A |
| A/A/B/A | A/B/B/B | B/A/B/B | B/B/A/B | | |

Other combinations are contemplated. The following discussion lists some agents that can be used as the "other therapy" in combination with agents of the present disclosure.

Elastase inhibitors find use in the treatment of NMO and IL-17-type MS. Inhibitors are known in the art, and include without limitation, sivelestat sodium hydrate (Ono Pharmaceutical); alpha1-antitrypsin; pafistatin-like protease inhibitors (de Marco, 2010), Peptides 31(7):1280-1260); Clitocybin D (Kim et al., 2009, J Microbiol Biotechnol. 19(10): 1139-41); marama bean inhibitor (Nadaraja et al., 2010, J Enzyme Inhib Med Chem. 25(3):377-82; AE-3763 (Inoue et al., 2009, Bioorg Med Chem. 17(21):7477-86); Isodeoxyhelicobasidin (Xu et al., 2009, J Antibiot 62(6):333-4); guamerin (Jo et al., 2008, Int Immunopharmacol. 8(7):959-66); elafin (Wang et al., 2008, Am J Respir Cell Mol Biol. 38(6):724-32); Bornyl (3,4,5-trihydroxy)-cinnamate (Steinbrecher et al., 2008, Bioorg Med Chem. 16(5):2385-90); and the like as known in the art. Other inhibitors of interest include antibodies specific for neutrophil elastase, anti-sense oligonucleotides, siRNA, shRNA, and the like.

Gro-alpha inhibitors are also of interest, e.g., antileukinate (see, for example Fujisawa et al. (1999) Melanoma res. 9(2):105-114. Other inhibitors of interest include antibodies specific for gro-alpha, anti-sense oligonucleotides, siRNA, shRNA, and the like.

In one embodiment, modulators of T cell and/or granulocyte activity are used in the treatment of inflammatory demyelinating disease of an IL-17 subtype, including subtypes of MS and NO. Patients may be classified according to cytokine subtype prior to administration of a granulocyte inhibitor, particularly MS patients. NO patients generally have an IL-17 type disease, and may be treated with a granulocyte inhibitor in the absence of cytokine profiling.

In some embodiments, the therapeutic agent is an elastase inhibitor, e.g., a small molecule inhibitor which may include without limitation, sivelestat sodium hydrate; a1-antitrypsin; pafistatin-like protease inhibitors; Clitocybin D); marama bean inhibitor; AE-3763; Isodeoxyhelicobasidin; guamerin; elafin; Bornyl (3,4,5-trihydroxy)-cinnamate; and the like as known in the art. Alternatively the therapeutic agent is an inhibitor of gro-alpha, e.g., peptides, small molecules, and the like.

In some embodiments, the other agents are antibodies specific for a granulocyte marker, e.g., elastase, gro-alpha, etc. The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

Corticosteroids have a short onset of action. Other disease modifying drugs take several weeks or months to demonstrate a clinical effect. These agents include methotrexate, leflunomide (Arava™), etanercept (Enbrel™), infliximab (Remicade™), adalimumab (Humira™), anakinra (Kineret™), rituximab (Rituxan™), CTLA4-Ig (abatacept), antimalarials, gold salts, sulfasalazine, d-penicillamine, cyclosporin A, cyclophosphamide azathioprine; and the like.

Antigen specific therapeutic methods include administration of an antigen or epitope specific therapeutic agent. One method to induce immune tolerance is tolerizing DNA vaccines (Garren et al., 2001, Immunity, 15:15-22; Robinson et al., 2003, Nature Biotechnology 21:1033-9). Tolerizing DNA vaccines are DNA plasmids containing the regulatory regions necessary for expression of the encoded cDNA in mammalian cells, and would be engineered to contain cDNA sequence encoding all or a portion of a targeted antigen in order to induce immune tolerance to the encoded epitopes. To enhance the ability of such plasmids to induce immune tolerance, the immunostimulatory CpG sequences (Krieg et al., 1998, Trends Microbiol. 6:23-27) can be reduced in number or completely removed from the plasmid vector. Additionally, immunoinhibitory GpG sequences can be added to the vector (see Ho et al., 2005, J. Immunology, 175:6226-34). Tolerizing DNA plasmids are delivered intramuscularly to induce immune tolerance to an antigen, thereby reducing T cell and autoantibody responses to reduce autoimmune destruction of the myelin sheath.

As an alternative, or in addition to DNA tolerization, specific peptides, altered peptides, or proteins may be administered therapeutically to induce antigen-specific tolerance to treat autoimmunity. Native peptides targeted by the autoimmune response can be delivered to induce antigen-specific tolerance (Gaur et al., Science 258:1491-4, 1992). Native peptides have been delivered intravenously to induce immune tolerance (Warren et al., J. Neurol. Sci. 152:31-8, 1997). Delivery of peptides that are altered from the native peptide, is also known in the art. Alteration of native peptides with selective changes of crucial residues (altered peptide ligands or "APL") can induce unresponsiveness or change the responsiveness of antigen-specific autoreactive T cells. In another embodiment, whole protein antigens targeted by the autoimmune response can be delivered to restore immune tolerance to treat autoimmunity (Critchfield et al., Science 263:1139, 1994).

E. Companion Diagnostics

In another aspect, the disclosure contemplates the application of companion diagnostic testing to determine the applicability of BAFF/APRIL-targeted therapies, as well as the inapplicability of interferon-based therapies. The inventor has determined that Th17-driven disease states (NMO, some MS) will not respond to interferon therapy and should respond favorably to BAFF/APRIL-targeted therapies. Thus, determining the levels of BAFF and/or APRIL in subjects will prove useful in guiding therapeutic options for these patients.

Assessment of expression levels of may be direct, as in the use of quantitative immunohistochemistry (IHC) or other antibody-based assays (Western blot, FIA, FISH, radioimmunoassay (MA), RIP, ELISA, immunoassay, immunoradiometric assay, a fluoroimmunoassay, an immunoassay, a chemiluminescent assay, a bioluminescent assay, a gel electrophoresis), or indirectly by quantitating the transcripts for these genes (in situ hybridization, nuclease protection, Northern blot or PCR, including RT-PCR). Relevant methodologies are discussed below.

1. Nucleic Acid-Based Methods

The present invention comprises methods of examining mRNA expression as a measure of target protein levels. mRNA is isolated from cancer cells according to standard methodologies (Sambrook et al., 1989). It may be desired to convert the RNA to a complementary DNA. In one embodiment, the RNA is whole cell RNA; in another, it is poly-A RNA. Normally, the nucleic acid is amplified.

Depending on the format, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994).

A variety of different assays are contemplated, including but not limited to, fluorescent in situ hybridization (FISH), Northern blotting, dot blot analysis, and of course PCR and RT-PCR. A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1990, each of which is incorporated herein by reference in its entirety.

Blotting techniques are well known to those of skill in the art. Southern blotting involves the use of DNA as a target, whereas Northern blotting involves the use of RNA as a target. Each technique provides different types of information, although cDNA blotting is analogous, in many aspects, to blotting or RNA species.

Briefly, a probe is used to target a RNA species that has been immobilized on a suitable matrix, often a filter of nitrocellulose. The different species should be spatially separated to facilitate analysis. This often is accomplished by gel electrophoresis of nucleic acid species followed by "blotting" on to the filter.

Subsequently, the blotted target is incubated with a probe (usually labeled) under conditions that promote denaturation and rehybridization. Because the probe is designed to base pair with the target, the probe will binding a portion of the target sequence under renaturing conditions. Unbound probe is then removed, and detection is accomplished as described above.

Products may be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by a labeled probe. The techniques involved are well known to those of skill in the art and can be found in many standard books on molecular protocols. See Sambrook et al. (1989). For example, chromophore or radiolabel probes or primers identify the target during or following amplification.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

In addition, the amplification products described above may be subjected to sequence analysis to identify specific kinds of variations using standard sequence analysis techniques. Within certain methods, exhaustive analysis of genes is carried out by sequence analysis using primer sets designed for optimal sequencing (Pignon et al, 1994). The present invention provides methods by which any or all of these types of analyses may be used. Using the sequences disclosed herein, oligonucleotide primers may be designed to permit the amplification of sequences that may then be analyzed by direct sequencing.

2. Immunodiagnostics

Antibodies of can be used in characterizing the survivin content of target cells through techniques such as ELISAs and Western blotting. The use of antibodies in the present invention in an ELISA assay is contemplated. For example, antibodies are immobilized onto a selected surface, preferably a surface exhibiting a protein affinity such as the wells of a polystyrene microtiter plate. After washing to remove incompletely adsorbed material, it is desirable to bind or coat the assay plate wells with a non-specific protein that is known to be antigenically neutral with regard to the test antisera such as bovine serum albumin (BSA), casein or solutions of powdered milk. This allows for blocking of non-specific adsorption sites on the immobilizing surface and thus reduces the background caused by non-specific binding of antigen onto the surface.

After binding of antibody to the well, coating with a non-reactive material to reduce background, and washing to remove unbound material, the immobilizing surface is contacted with the sample to be tested in a manner conducive to immune complex (antigen/antibody) formation.

Following formation of specific immunocomplexes between the test sample and the bound antibody, and subsequent washing, the occurrence and even amount of immunocomplex formation may be determined by subjecting same to a second antibody having specificity for a tumor suppressor that differs the first antibody. Appropriate conditions preferably include diluting the sample with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hr, at temperatures preferably on the order of about 25° to about 27° C. Following incubation, the antisera-contacted surface is washed so as to remove non-immunocomplexed material. A preferred washing procedure includes washing with a solution such as PBS/Tween®, or borate buffer.

To provide a detecting means, the second antibody will preferably have an associated enzyme that will generate a color development upon incubating with an appropriate chromogenic substrate. Thus, for example, one will desire to contact and incubate the second antibody-bound surface with a urease or peroxidase-conjugated anti-human IgG for a period of time and under conditions which favor the development of immunocomplex formation (e.g., incubation for 2 hr at room temperature in a PBS-containing solution such as PBS/Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectrum spectrophotometer.

The preceding format may be altered by first binding the sample to the assay plate. Then, primary antibody is incubated with the assay plate, followed by detecting of bound primary antibody using a labeled second antibody with specificity for the primary antibody.

Antibodies can also find use in immunoblots or Western blot analysis. The antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. Immunologically-based detection methods for use in conjunction with Western blotting include enzymatically-, radiolabel-, or fluorescently-tagged secondary antibodies against the tumor suppressor are considered to be of particular use in this regard.

F. Kits

For use in the applications described herein, kits are also within the scope of the disclosure. Such kits can comprise a carrier, package or container that is compartmentalized to receive one or more containers such as vials, tubes, and the like, each of the container(s) comprising one of the separate elements to be used in the methods disclosed herein. The kit of the invention will typically comprise the container described above and one or more other containers comprising materials desirable from a commercial end user standpoint, including buffers, diluents, filters, and package inserts with instructions for use. In addition, a label can be provided on the container to indicate that the composition is used for a specific therapeutic or diagnostic application, and can also indicate directions for either in vivo or in vitro use, such as those described above. Directions and or other information can also be included on an insert which is included with the kit. In particular, kits according to the present invention contemplate the assemblage of agents for assessing leves of the biomarkers discussed above along with one or more of a therapeutic and/or a reagent, as well as controls for assessing the same.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials and Methods

Induction of TH1- and TH17-EAE. To induce TH1- and TH17 EAE, the inventor will immunize donor C57BL/6 or SJL mice with $MOG_{35-55}$ or $PLP_{139-151}$ peptides, respectively, in complete Freund's adjuvant. Ten days post immunization, spleens and lymph nodes from these mice will be harvested and cultured for 3 days with the immunizing antigen in conditions favoring TH1 (IL-12 and anti-IL-4) or TH17 (IL-23, anti-IFNγ and anti-IL-4) differentiation. After culturing, 5-10×10$^6$ cells from each condition will be injected intravenously into healthy recipient mice of the same background. Paralysis follows the typical EAE progression and mice will be monitored and scored as follows: 0, normal; 1, tail paralysis; 2, hind limb weakness; 3, complete hind limb paralysis; 4, hind limb paralysis with forelimb weakness and 5, moribund or death (see FIG. 1A).

Assess the Dynamics of BAFF and APRIL Expression. The first goal of this objective is to assess the expression of BAFF and APRIL throughout the course of TH1 and TH17-EAE. The inventor has already shown that the transcription of BAFF and APRIL genes are elevated in the spinal cords of TH17-EAE compared to TH1-EAE (see FIG. 1B). However, both BAFF and APRIL are expressed as membrane bound molecules which become activated upon cleavage with furin-like proteases. Therefore, the inventor will measure protein expression of BAFF and APRIL in spleens, serum, brain and spinal cord by western blot. This will allow us to confirm that the protein is indeed translated in these tissues during disease and also assess the ratio of membrane bound (inactive) and cleaved (active) forms of these molecules.

Characterization of B-cell subsets in TH1 and TH17 EAE. The second goal of this objective is to assess the tissue distribution of B-cell subsets during TH1 and TH17 EAE. The inventor will phenotype B-cell subsets in blood, spleen, lymph nodes, and central nervous system (CNS) at four time points during TH17 and TH1-EAE. The time points will be prior to onset of paralysis, at the time of disease onset, at the peak of disease and during the chronic phase of the disease. B-cell subsets will be identified by flow cytometry with the following scheme. Newly developed B-cells will be defined as $CD19^+IgM^{high}IgD^{low}CD93^+$, mature follicular B-cells as $CD19^+IgM^{low}IgD^+CD1d^{low}CD21/35^{low}$; regulatory B-cells as $CD19^+CD1d^{high}CD21^{high}IgM^{high}IgD^{-/-}CD5^+$; germinal center B-cells as $CD19^+PNA^+GL7^+$; and plasmablasts/cells as $B220^{+/-}CD138^+CD267^+$. In addition, the inventor will assess the development of anti-myelin antibodies throughout the course of EAE by ELISA.

Statistical Analysis. Results from these experiments will be presented as means+/− one standard deviation, and significance will be determined by a two-tailed Student's t test or one way ANOVA.

Treatment of TH1 and TH17 EAE with TACI-Ig and Anti-APRIL. In this study, the inventors presents data (n=3 mice/group) showing that intraperitoneal injections of TACI-Ig (100 μg/dose every 3$^{rd}$ day) reverses the clinical course of TH17-EAE when treatment is initiated at the peak of acute disease (see FIG. 2A). The inventor will expand this work to include TACI-Ig and anti-APRIL to treat both TH1 and TH17 EAE models. In addition, the inventor will use PBS, human IgG (control for TACI-Ig) and mouse IgG2b (control for anti-APRIL) as appropriate treatment controls. Treatments (100 μg of treatment/dose) will be administered every 3 days beginning at the peak of EAE and continued through the course of the experiment.

Assessment of Treatment Effects. The inventor will evaluate EAE severity by monitoring clinical scores. The degree of inflammation and demyelination in brains and spinal cords from these mice will be assessed by staining paraffin embedded sections with hematoxylin and eosin (to assess inflammatory infiltrates) and Luxol Fast Blue (to assess myelin integrity). The inventor will also determine effects these treatments have on B-cell development and function. Specifically, the following will be assessed: (1) Changes in B-cell cytokines, BAFF and APRIL, by qPCR, ELISA and/or Western blot; (2) Changes in B-cell subsets infiltrating brain and spinal cords by flow cytometry; and (3) Changes in the development of anti-myelin autoantibodies in serum by ELISA.

Outcome Measures and Statistical Analysis. For all EAE experiments, differences in clinical outcomes will be determined by Mann-Whitney test, with $p<0.05$ considered significant. ELISA, flow cytometry and qPCR results will be presented as means+/− one standard deviation, and significance will be determined by a two-tailed Student's t test or one-way ANOVA.

Power Calculations Determining Number of Mice per Experiment. Assuming that the variability in the proposed experiments will be similar to that of the 5 most recent EAE experiments, 11 mice will be required per experimental arm in order to detect a true difference of 1 normalized unit at a significance level of 0.05 and power of 0.83 with a standard deviation of 0.3 units for each group of animals. The inventor intends to repeat each experiment two to three times.

Example 2—Results

The inventor's lab has developed and characterized two EAE models that mimic different MS patient populations, TH1-induced EAE and TH17-induced EAE. The inventor initially reported that TH1-EAE mimics an MS phenotype that responds well to IFN-β treatment, whereas the TH17-EAE resembles patients that are IFN-β non-responders (Axtell et al., 2010). The inventor further characterized the phenotypic differences of these two models and found that mice with TH17-EAE have increased disease severity (FIG. 1A) and increased neutrophil infiltration in the CNS compared to mice with TH1-EAE (Herges et al., 2012). The inventor now has data demonstrating that B-cells have differing functions in these two EAE models. The inventor observed that the expression levels of BAFF and APRIL RNA are significantly elevated in the spinal cords of mice with TH17-EAE compared to mice with TH1-EAE (FIG. 1B). In addition, the inventor found that the frequency of $CD19^+$ B-cells were elevated in spinal cords of TH17-EAE compared to TH1-EAE, although frequencies of $CD4^+$ T-cells were equivalent in both EAE models (FIGS. 1C-D).

Figure 2A:
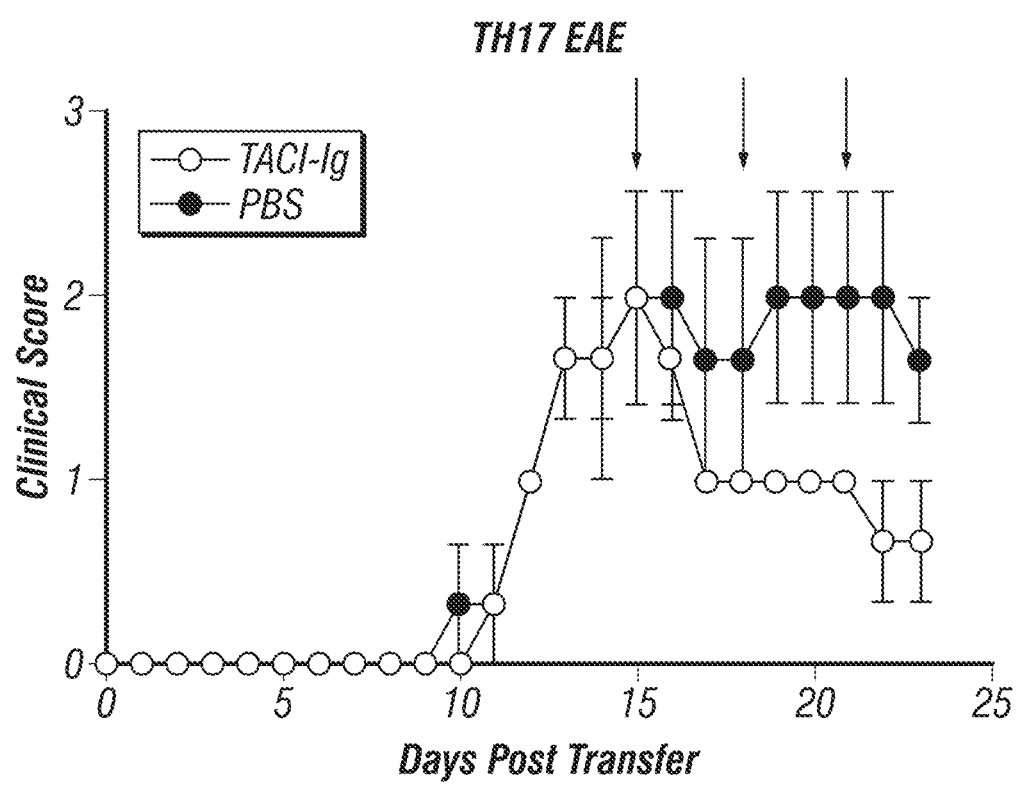
FIGS. 2A-C. Effects of TACI-Ig on TH17-EAE.
Figure 2B:
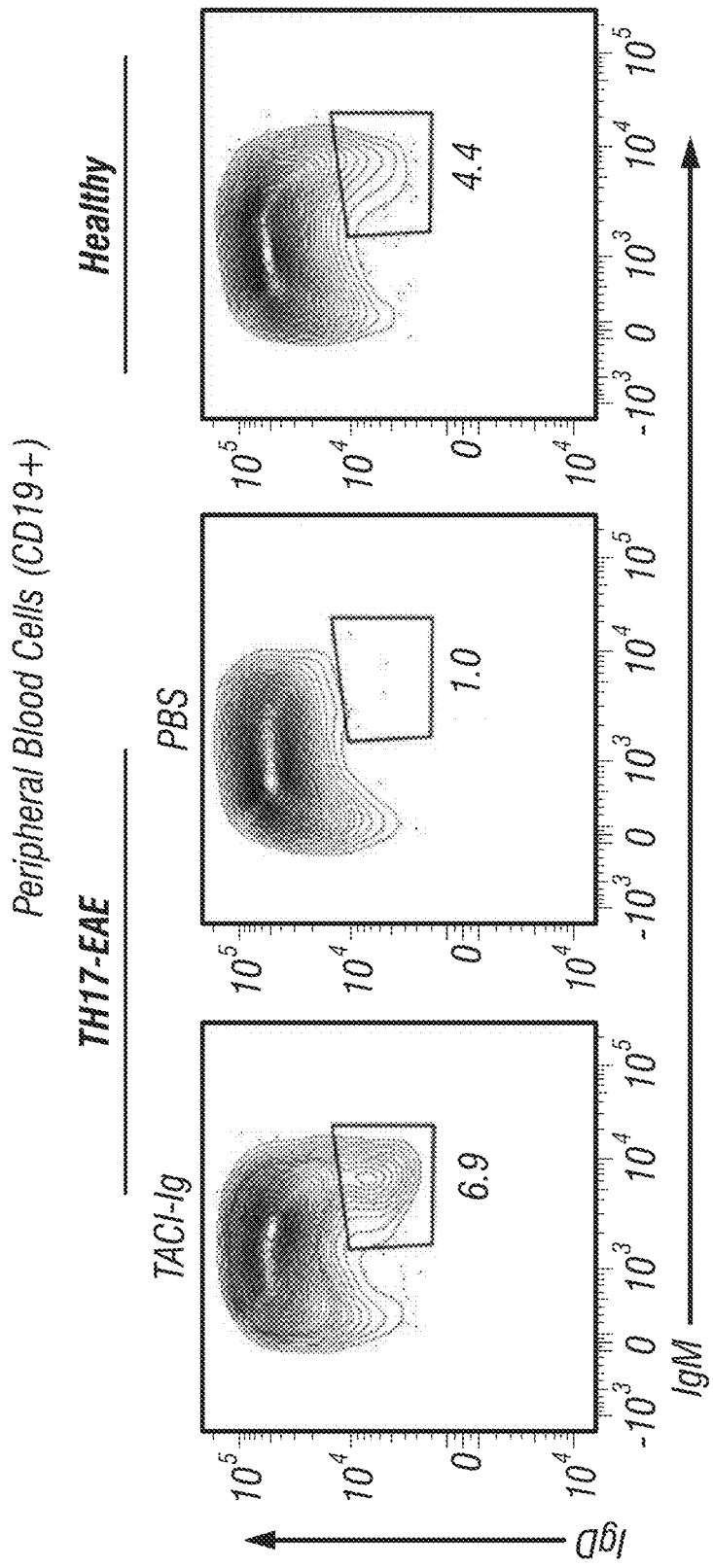
Figure 2C:
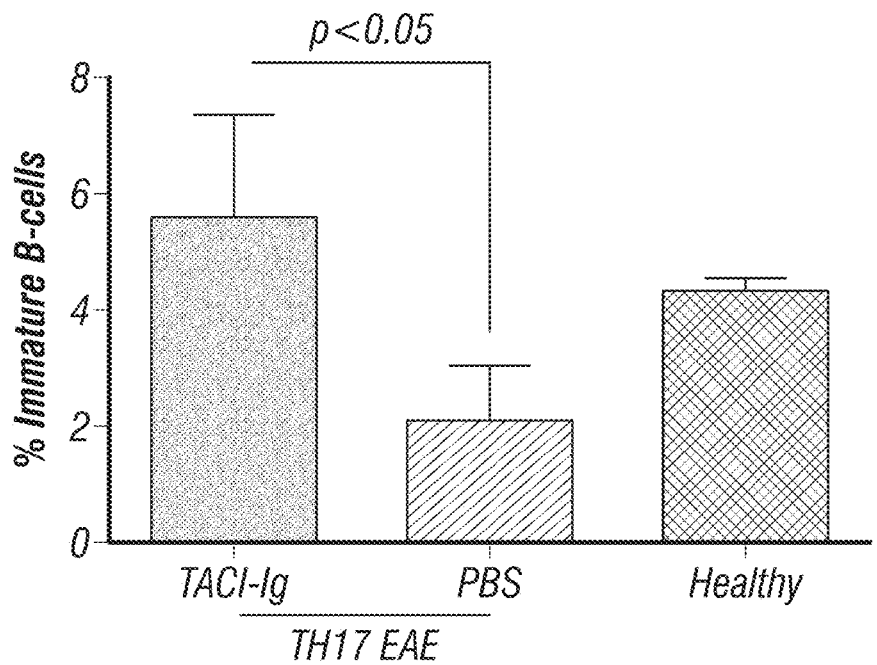

Since BAFF, APRIL and B-cells were elevated in the spinal cords of mice with TH17-EAE, the inventor assessed the effects recombinant TACI-Ig treatment had on this EAE model. The inventor treated TH17-EAE with TACI-Ig (100 μg/dose, N=3) or PBS (N=3) every 3 days beginning at the peak of acute disease. The inventor found that mice treated with TACI-Ig had a greater recovery from paralysis compared to the PBS treated mice (FIG. 2A). The inventor also assessed the effects this treatment had B-cell populations in the peripheral blood. The inventor found that TACI-Ig treatment restored the frequency of immature B-cells (Ig-$M^{high}$IgD$^{low}$) in the blood to levels that are comparable to healthy mice.

Figures 3A, 3B:
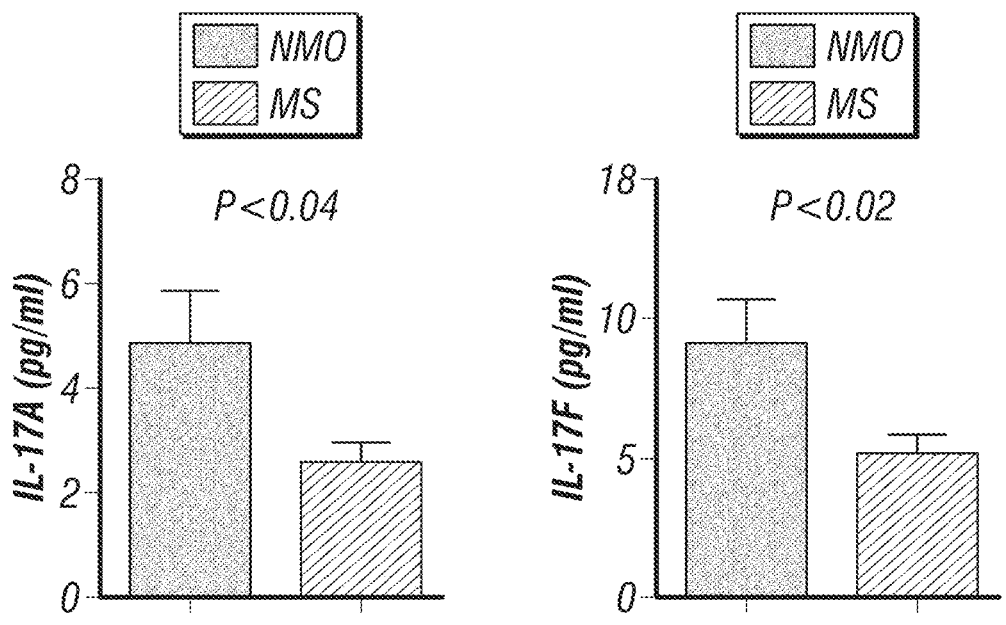
FIGS. 3A-B. Serum levels of TH17 cytokines are elevated in NMO patients compared to MS. The TH17 cytokines IL-17A (FIG. 3A) and IL-17F (FIG. 3B) were measured using a luminex multiplex assay. Significance was determined by a student's T-test.
Figure 4A:
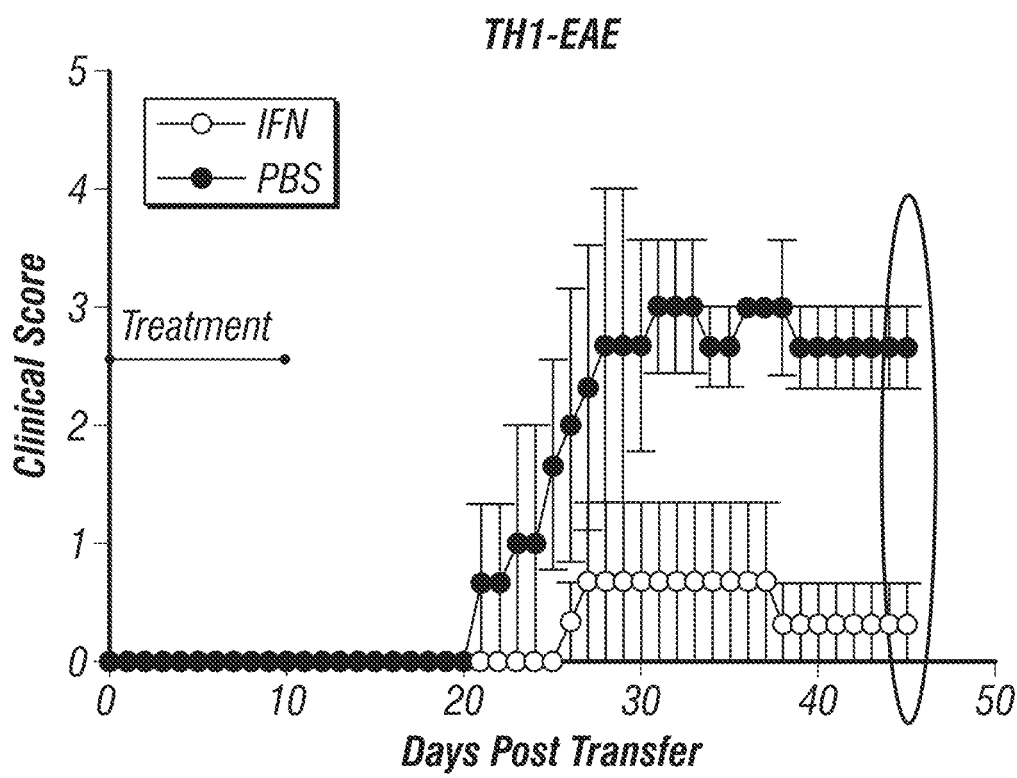
FIGS. 4A-D. IFN-β treatment is therapeutic in TH1-EAE and inflammatory in TH17-EAE. Mice with TH1-EAE (FIG. 4A) or TH17-EAE (FIG. 4B) were treated every second day with 1000 units of IFN-β from day 0-day 10 and diseases scores were monitored until day 45. Inflammation and demyelination in spinal cords from mice with TH1 (FIG. 4C) and TH17 (FIG. 4D) were assessed by staining paraffin embedded sections with hematoxylin and eosin (to assess inflammatory infiltrates) and Luxol Fast Blue (to assess myelin integrity).
Figure 4B:
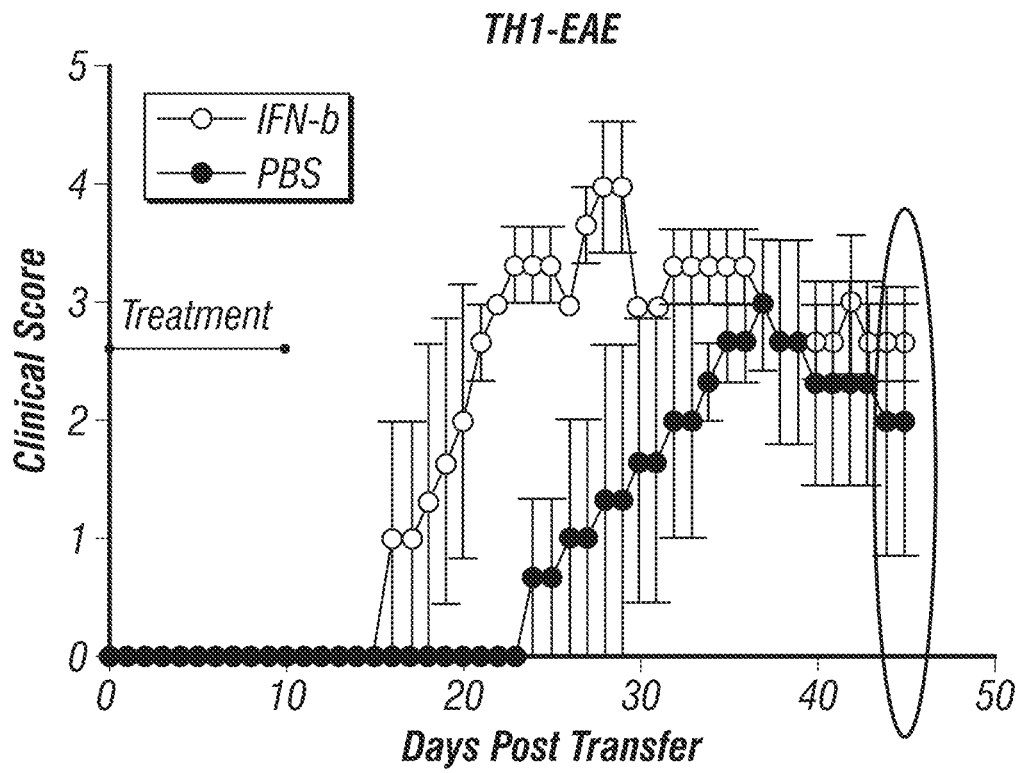
Figure 4C:
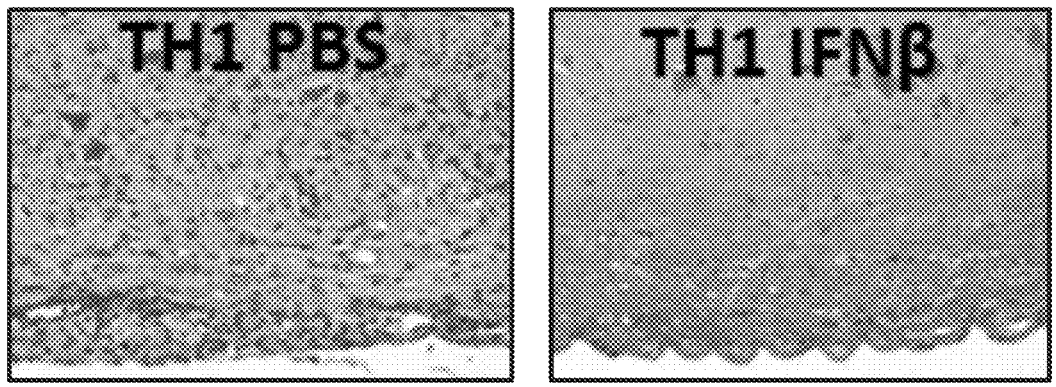
Figure 4D:
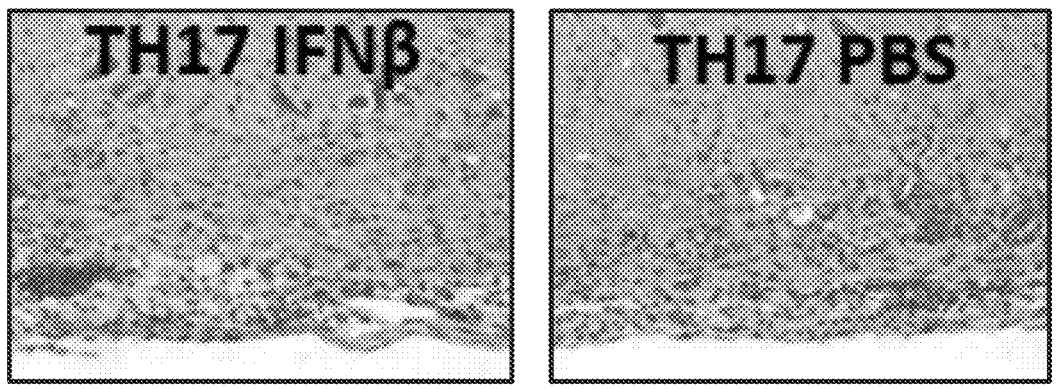
Figure 5A:
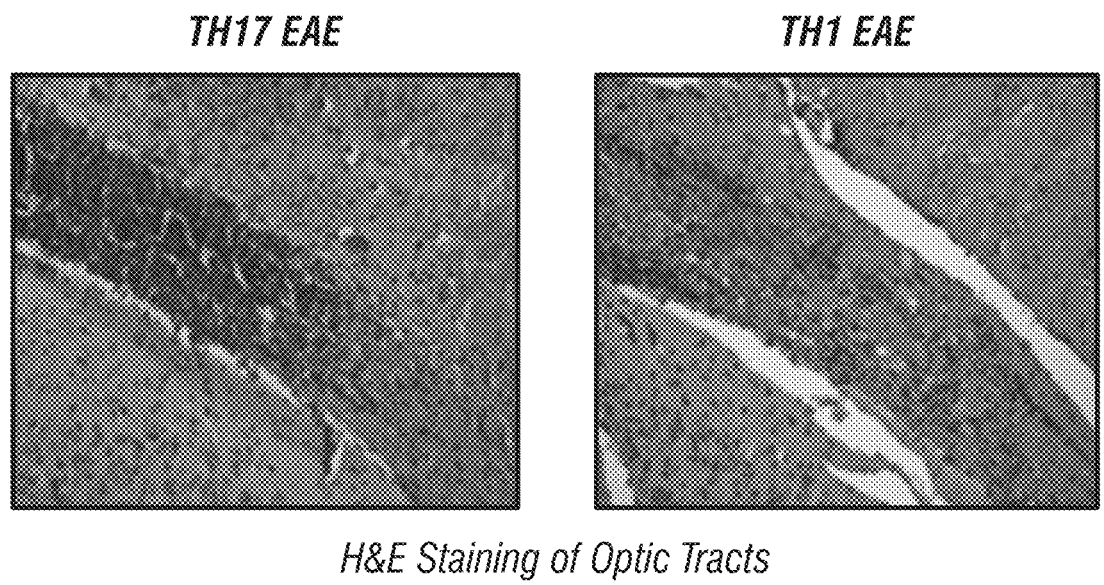
FIGS. 5A-B. TH17-EAE has severe optic neuritis and visual deficits than TH1-EAE.
Figure 5B:
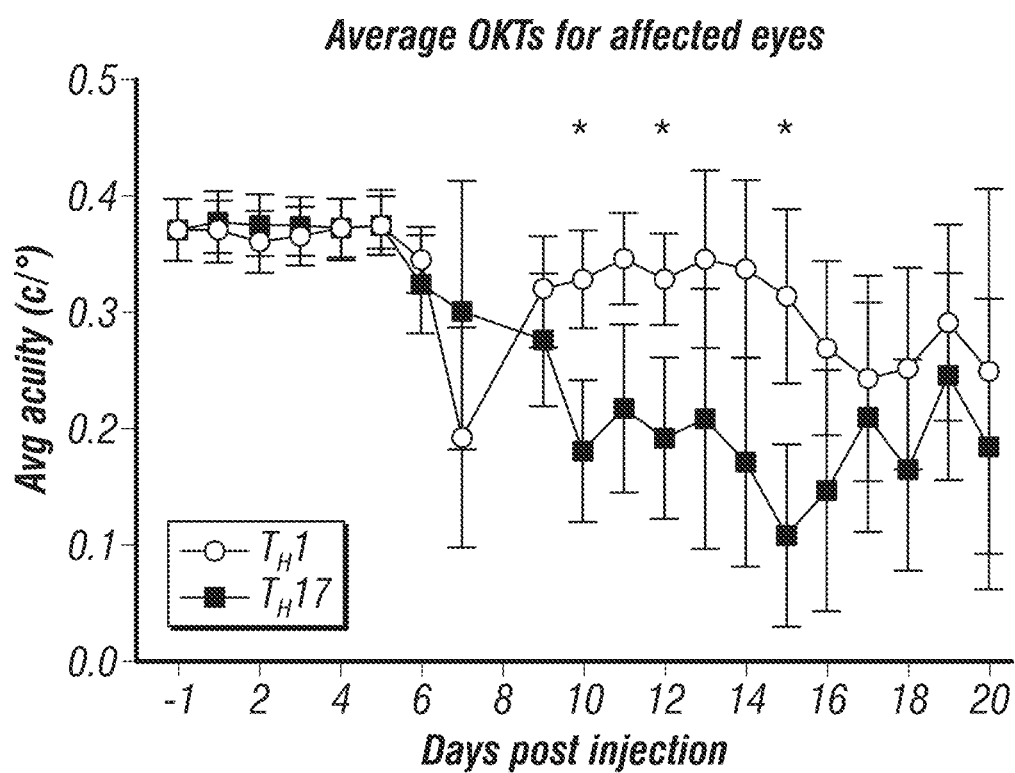
Figure 6A:
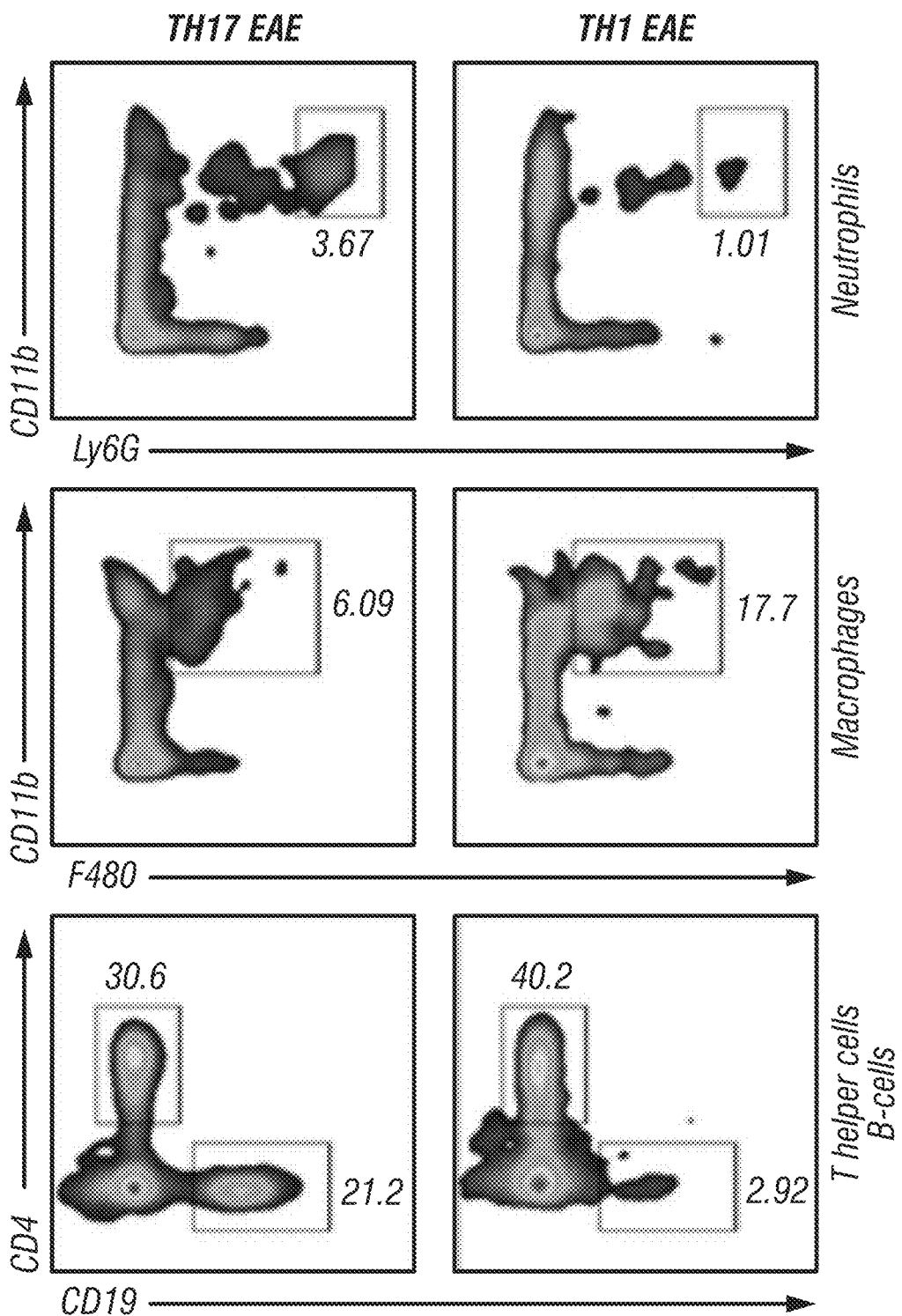
FIGS. 6A-B. TH17-EAE has increased neutrophils and B-cells in the inflamed spinal cords compared to TH1 EAE.
Figure 6B:
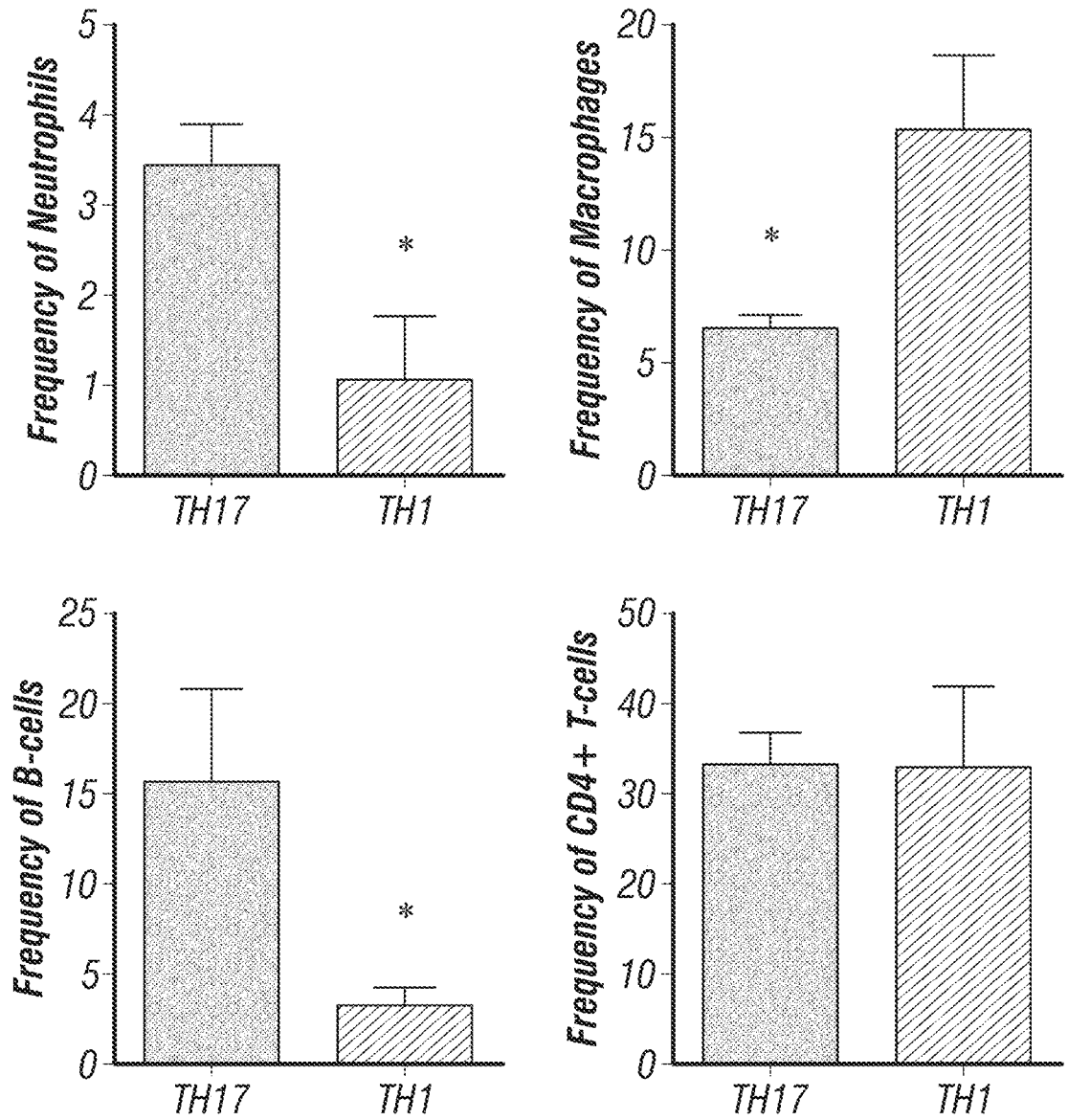
Figure 7A:
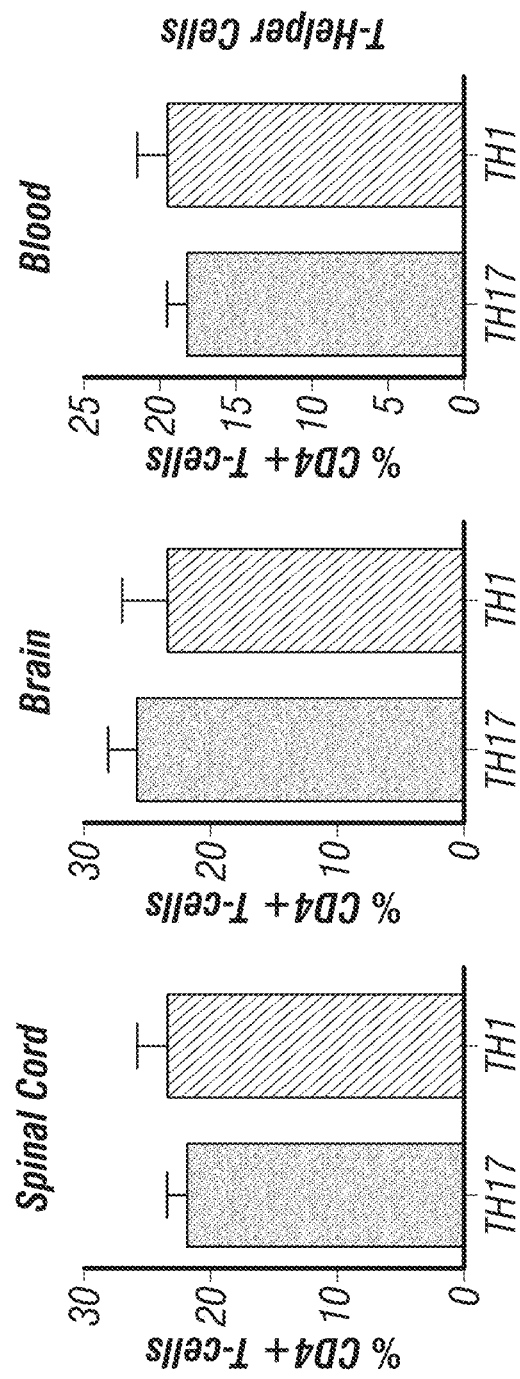
FIGS. 7A-C. Comparison of the frequency (FIG. 7A) of CD4 T helper cells, (FIG. 7B) Neutrophils and (FIG. 7C) B-cells in the spinal cord, brain and blood from mice with TH1-EAE and TH17-EAE. P-values were determined using a Mann-Whitney U test with * p<0.05, p<0.01, *p<0.001, FIG. 8. BAFF and APRIL expression in peripheral blood cells, brain and spinal cords of mice with TH1-EAE or TH17. Statistical analysis was performed using a students t-test with p-values *<0.05 and **<0.01.
Figure 7B:
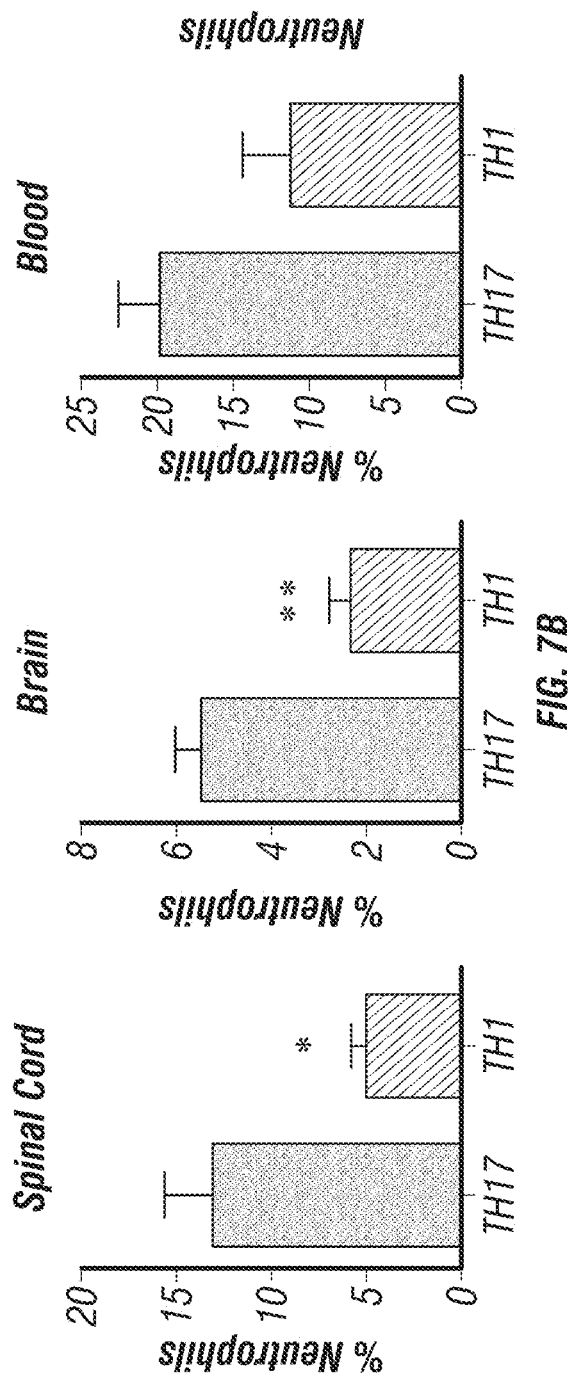
Figure 7C:
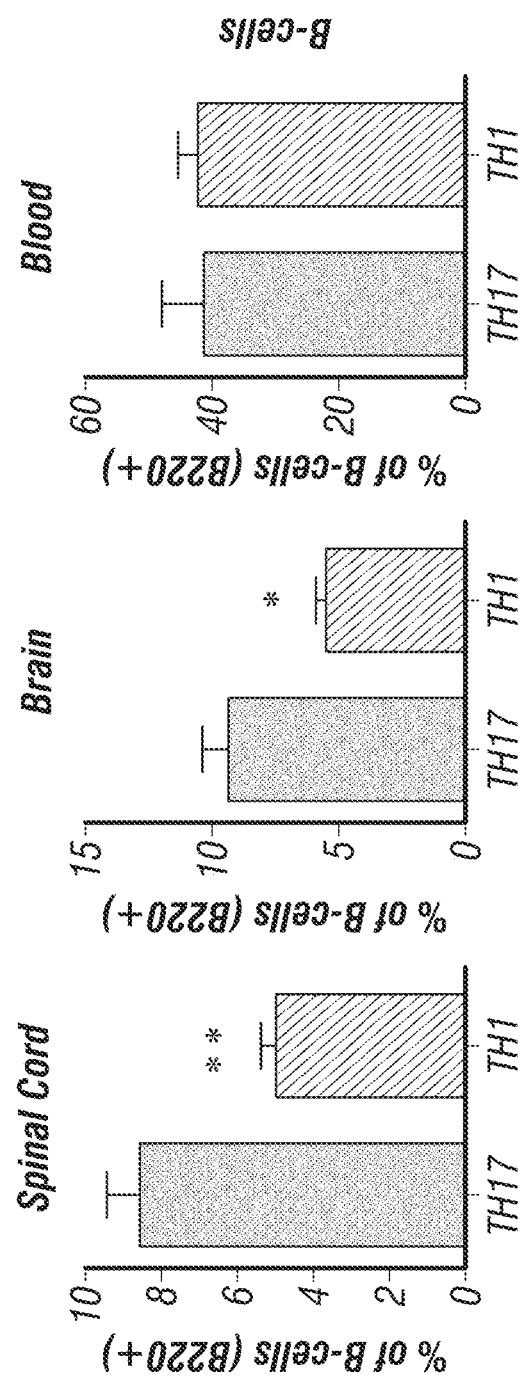
Figure 8:
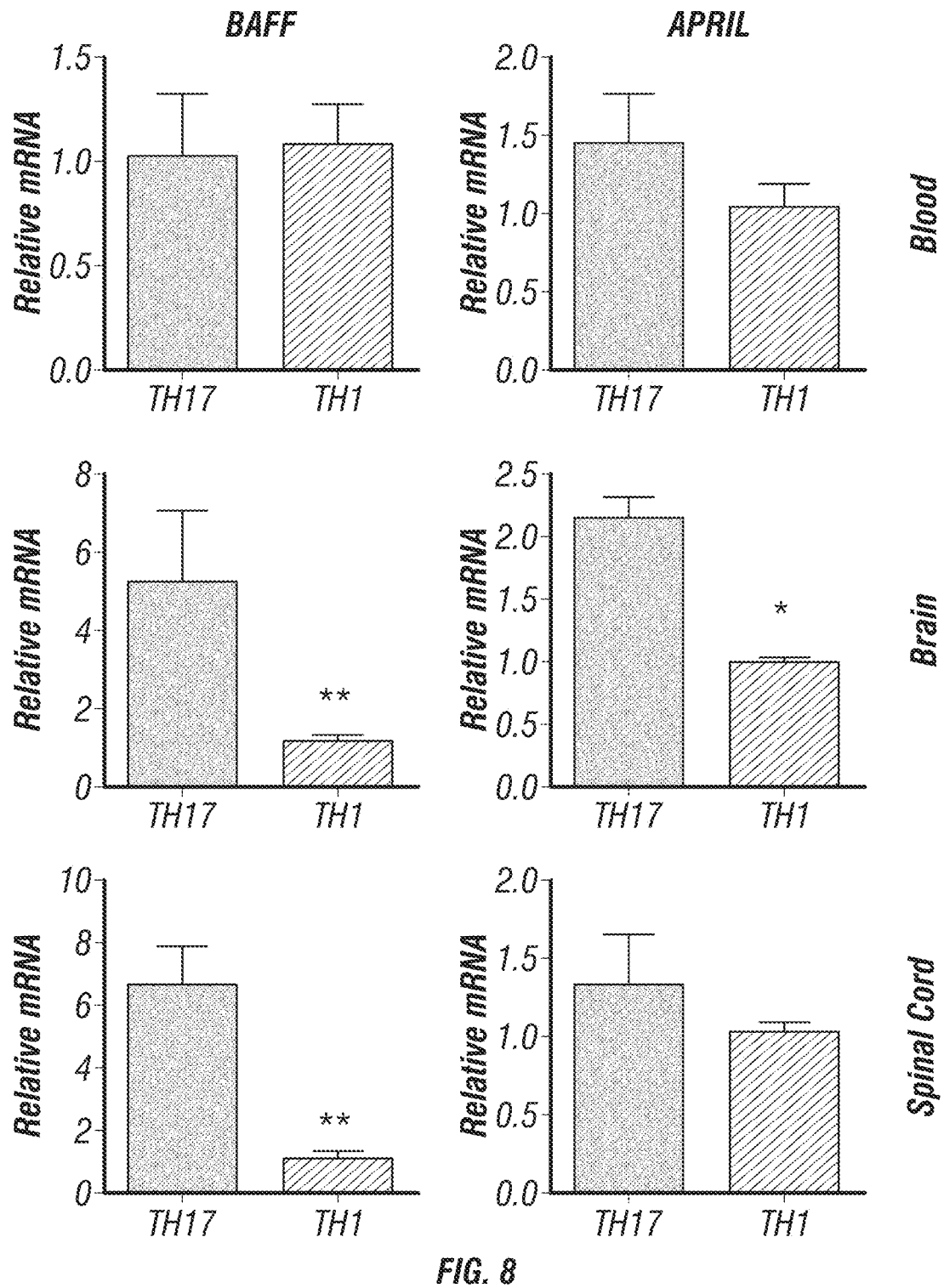
Figure 9A:
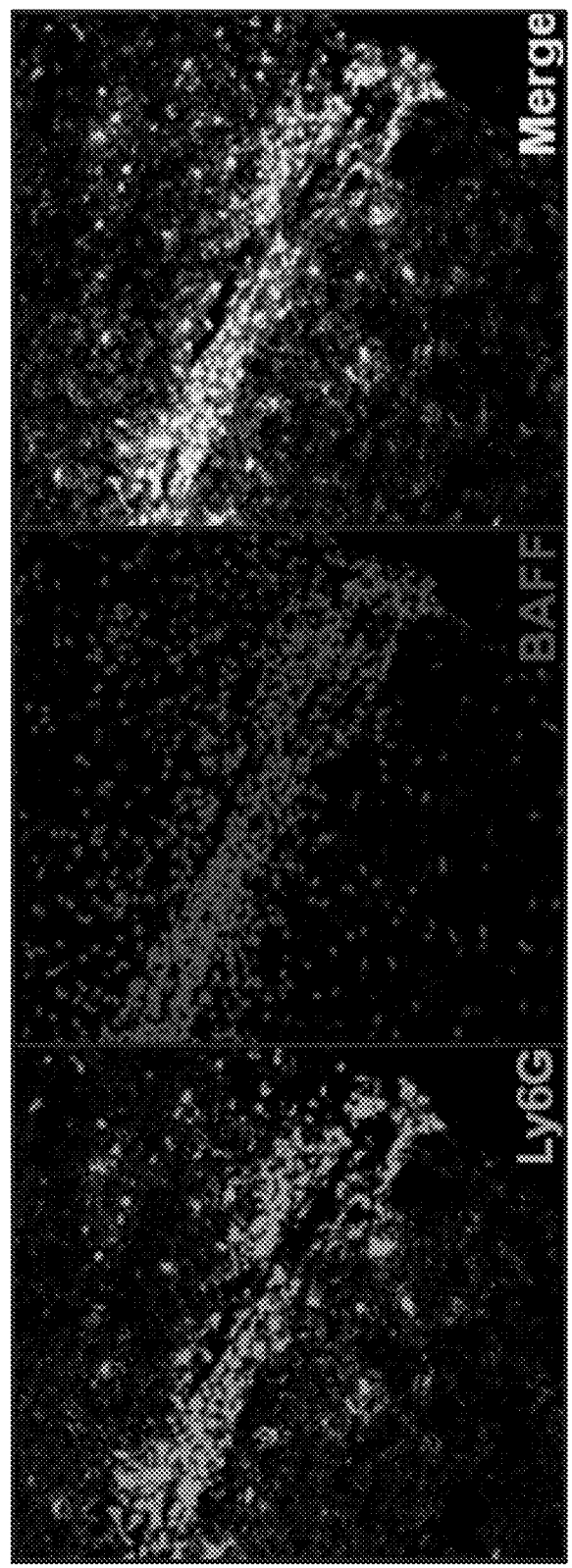
FIGS. 9A-B. TH17-EAE spinal chord analysis for BAFF expression.
Figure 9B:
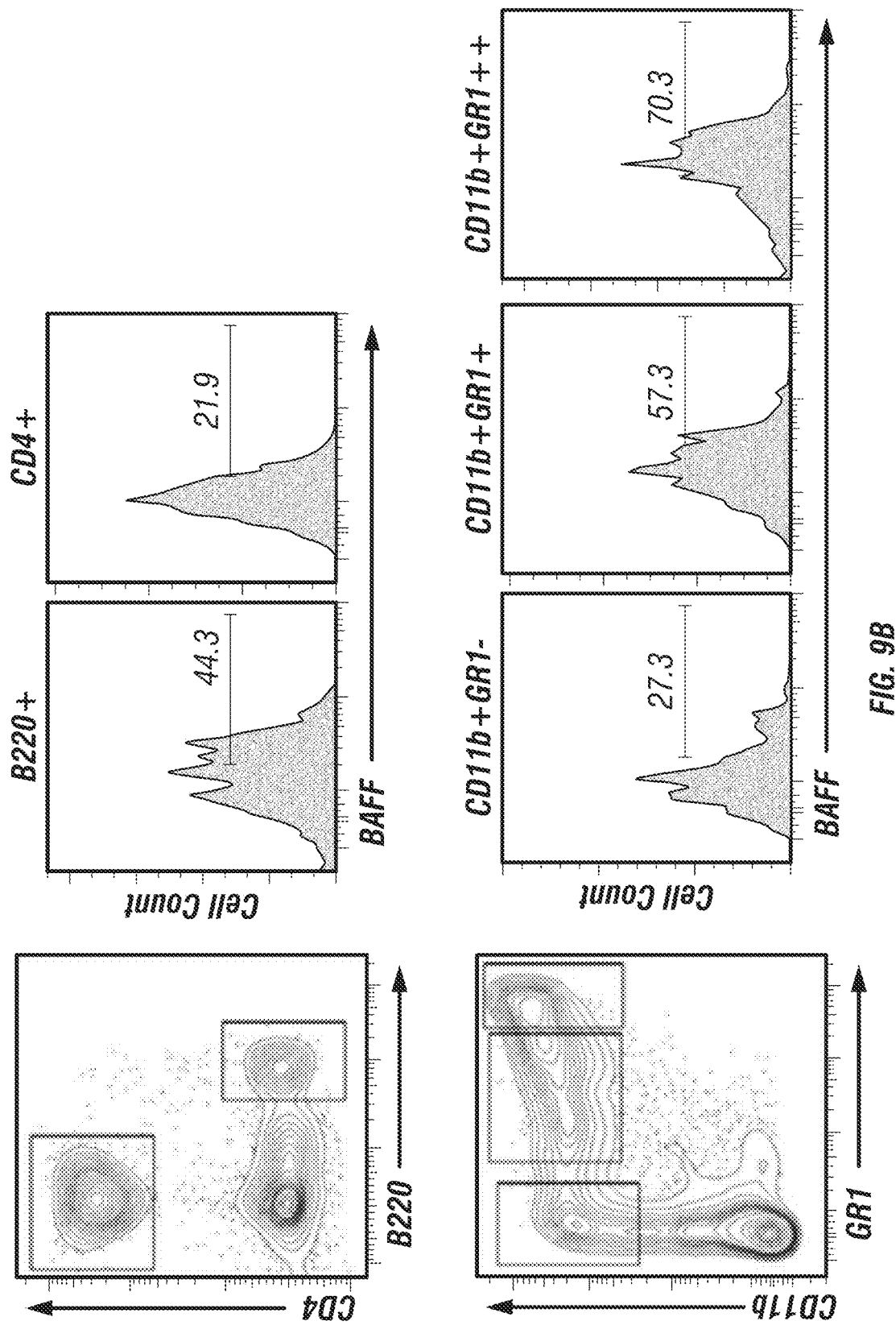
Figure 10:
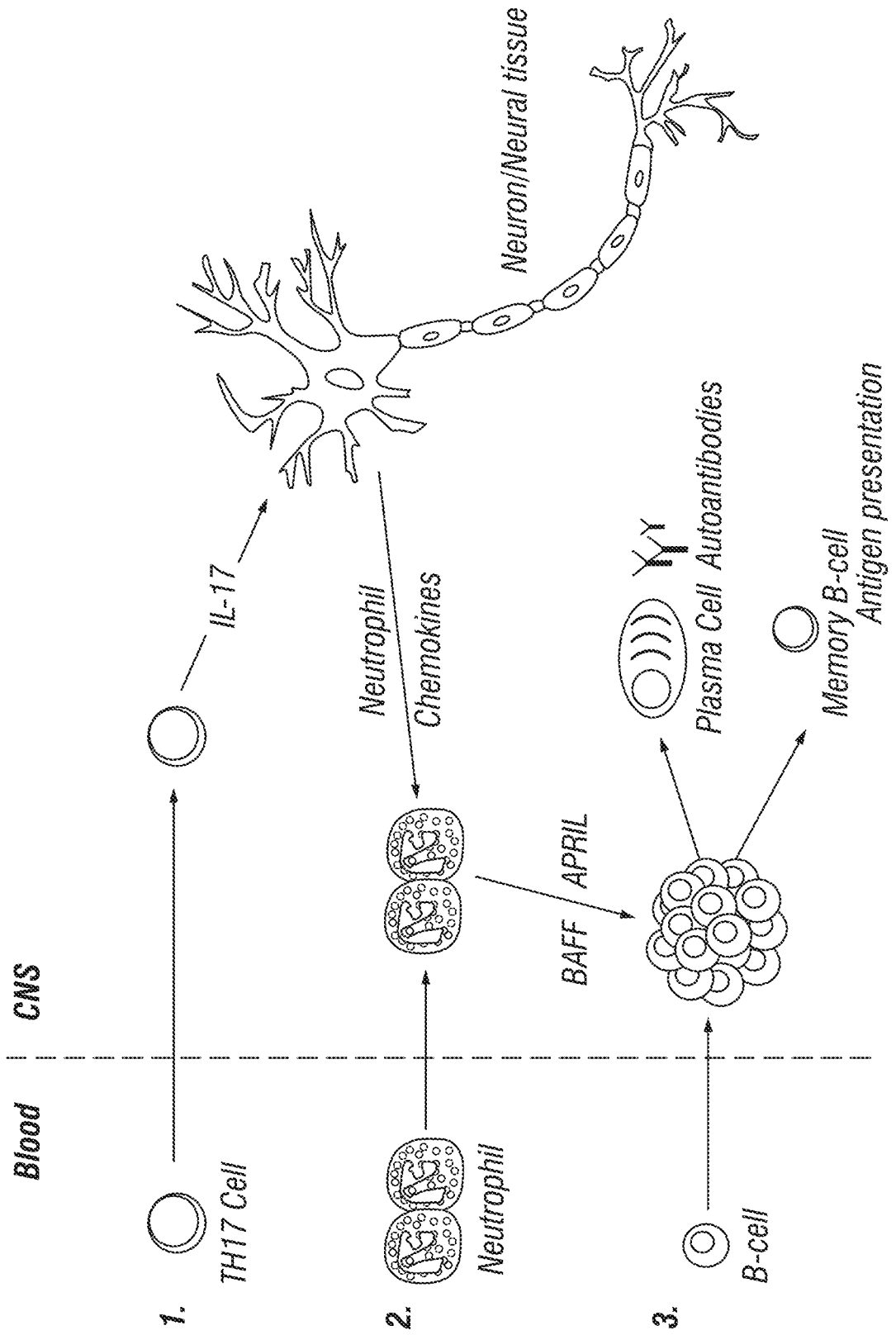
FIG. 10. Cellular and molecular cascade of events that occurs in TH17 mediated neuro-inflammation. 1) TH17 cells infiltrate the CNS and secrete TH17 cytokines (IL-17) which induces the expression of neutrophil chemokines within the inflamed tissue. 2) Neutrophils migrate to the CNS. 3) Neutrophils express high levels of BAFF and APRIL which drives the proliferation of B-cells in the CNS. B-cells then mediated inflammation by antigen presentation to newly immigrated T-cells and/or by the production of autoantibodies.

The inventors found that TH17-EAE represents a disease phenotype that is similar to NMO where-as TH1-EAE represents MS. First, they found that the TH17 cytokines IL-17A and IL-17F are elevated in the serum from NMO patients compared to MS patients (FIGS. 3A and B). Second, they found that like NMO, IFN-β treatment worsened disease TH17-EAE and conversely, like MS IFN-β reduced TH1-EAE (FIG. 4A-D). Third, like NMO, they found that TH17-EAE have more severe optic neuritis (FIG. 5A) and increased visual deficits (FIG. 5B) that TH1-EAE. Finally, they found that like NMO, the neutrophils comprise a significant proportion of the inflammatory cells that infiltrate the central nervous system in TH17-EAE but not TH1-EAE (FIGS. 6 and 7B). In addition to neutrophils, they found that B-cells are a predominant infiltrate in CNS of TH17-EAE compared to TH1-EAE (FIGS. 6 and 7C). Concordantly, they found that the expression of BAFF and APRIL, which are cytokines that drive the proliferation and survival of B-cells, are significantly increased in TH17-EAE compared to TH1-EAE (FIG. 8). The inventors now find that the cell-type that expresses the majority of BAFF and APRIL in the lesions of TH17-EAE are neutrophils (FIGS. 9A-B). These data demonstrates a pathogenic cascade of events that occurs in TH17 mediated neuro-inflammation such as NMO (FIG. 10). First, TH17 cells infiltrate the CNS and secrete TH17 cytokines (IL-17) which induces the expression of neutrophil chemokines within the inflamed tissue. Neutrophils, that are expressing high levels of BAFF and APRIL, then migrate to the CNS and induce the proliferation of B-cells in a BAFF dependent manner. These B-cells then can either present antigen to newly immigrated T-cells or express autoantibodies to promote more inflammation.

Example 3—Discussion

The data presented here support the hypothesis that B-cells, BAFF and APRIL are inflammatory in TH17 mediated diseases and are conversely anti-inflammatory in TH1 mediated diseases. The expanded studies will definitively prove this hypothesis and in doing so it will provide insights into (i) the inflammatory and regulatory functions B-cells have in autoimmune diseases; (ii) the role differential roles BAFF and APRIL play in TH1- and TH17-induced inflammation; and (iii) the clinical effects of blocking BAFF and APRIL in MS patients.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. Certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

V. REFERENCES

The following references, to the extent that they provide exemplary procedural or other details supplementary to those set forth herein, are specifically incorporated herein by reference:

U.S. Pat. No. 4,683,195
U.S. Pat. No. 4,683,202
U.S. Pat. No. 4,800,159
U.S. Pat. No. 5,279,721
Axtell et al., *Nat Med.* 16(4):406-12, 2010.
Bellus, *J. Macromol. Sci. Pure Appl. Chem.*, A31(1): 1355-1376, 1994.
Herges et al., *Mult Scler.* 18(4):398-408, 2012.
Innis et al., *Proc. Natl. Acad. Sci. USA,* 85(24):9436-9440, 1988.
McDonald et al., *Ann. Neurol.,* 50:121-127, 2001.
Remington's Pharmaceutical Sciences, 15$^{th}$ Ed., 1035-1038 and 1570-1580.
Sambrook et al., In: *Molecular Cloning*, Cold Spring Harbor Laboratory Press, Cold Spring Harbor, N Y, 1989.

What is claimed is:

1. A method for treating a subject having interferon-resistant multiple sclerosis (MS) comprising administering atacicept to said subject.
2. The method of claim 1, wherein administering comprises intravenous, intra arterial, subcutaneous, topical or oral administration.
3. The method of claim 1, wherein said atacicept is administered more than once.
4. The method of claim 3, wherein said atacicept is administered chronically.
5. The method of claim 1, further comprising administering to said subject a second MS therapy.
6. The method of claim 5, wherein said second MS therapy is selected from the group consisting of an elastase inhibitor, a gro-alpha inhibitor, corticosteroids, glatiramer acetate, mitoxantrone, natalizumab, fingolimod, teriflunomide and dimethyl fumarate.
7. The method of claim 1, wherein said subject suffers from vision impairment, muscle impairment or both.
8. The method of claim 7, wherein said subject, following treatment, exhibits an improvement in vision impairment, muscle impairment or both.
9. The method of claim 1, wherein said subject is a non-human mammal.
10. The method of claim 1, wherein said subject is a human.

* * * * *